United States Patent
Mcadam et al.

(10) Patent No.: US 12,274,824 B2
(45) Date of Patent: Apr. 15, 2025

(54) AEROSOL PROVISION SYSTEM

(71) Applicant: NICOVENTURES TRADING LIMITED, London (GB)

(72) Inventors: Kevin Gerard Mcadam, London (GB); Connor Bruton, London (GB)

(73) Assignee: NICOVENTURES TRADING LIMITED, London (GB)

(*) Notice: Subject to any disclaimer, the term of this patent is extended or adjusted under 35 U.S.C. 154(b) by 1005 days.

(21) Appl. No.: 15/764,612

(22) PCT Filed: Sep. 30, 2016

(86) PCT No.: PCT/GB2016/053051
§ 371 (c)(1),
(2) Date: Mar. 29, 2018

(87) PCT Pub. No.: WO2017/055866
PCT Pub. Date: Apr. 6, 2017

(65) Prior Publication Data
US 2018/0279679 A1  Oct. 4, 2018

(30) Foreign Application Priority Data
Oct. 1, 2015 (GB) ........................... 1517361

(51) Int. Cl.
*A24F 47/00* (2020.01)
*A24F 40/42* (2020.01)
(Continued)

(52) U.S. Cl.
CPC ............ *A61M 15/06* (2013.01); *A24F 40/42* (2020.01); *A24F 40/46* (2020.01); *A61M 11/042* (2014.02);
(Continued)

(58) Field of Classification Search
CPC ........ A24F 40/42; A24F 47/008; A24F 40/46; A24F 40/10; A61M 11/042; A61M 15/06;
(Continued)

(56) References Cited

U.S. PATENT DOCUMENTS 228,598 A  6/1880 Buckley
353,327 A  11/1886 Randolph
(Continued)

FOREIGN PATENT DOCUMENTS

AT  507187 A4  3/2010
AT  507187 B1  3/2010
(Continued)

OTHER PUBLICATIONS

Vaperanks, *Luxury Customization Company Launches 24ct-Gold-Plated E-Cigarettes*, vaperanks.com, as available from: http://vaperanks.com/luxury-customization-company-launches-24ct-gold-plated-e-cigarette/, as accessed on Feb. 4, 2016, 3 pages.
(Continued)

*Primary Examiner* — Dionne W. Mayes
(74) *Attorney, Agent, or Firm* — Husch Blackwell

(57) ABSTRACT

The present disclosure relates to an aerosol provision cartridge for use with an aerosol provision system, the cartridge including a liquid storage region including a source liquid, the source liquid including nicotine and at least one acid; an aerosol generating region in fluid communication with the liquid storage region; and one or more metallic components, located substantially outside of the aerosol generating region and liquid storage region, wherein at least one of the metallic components has a coating comprising silver and/or gold.

16 Claims, 5 Drawing Sheets

Figure 1:
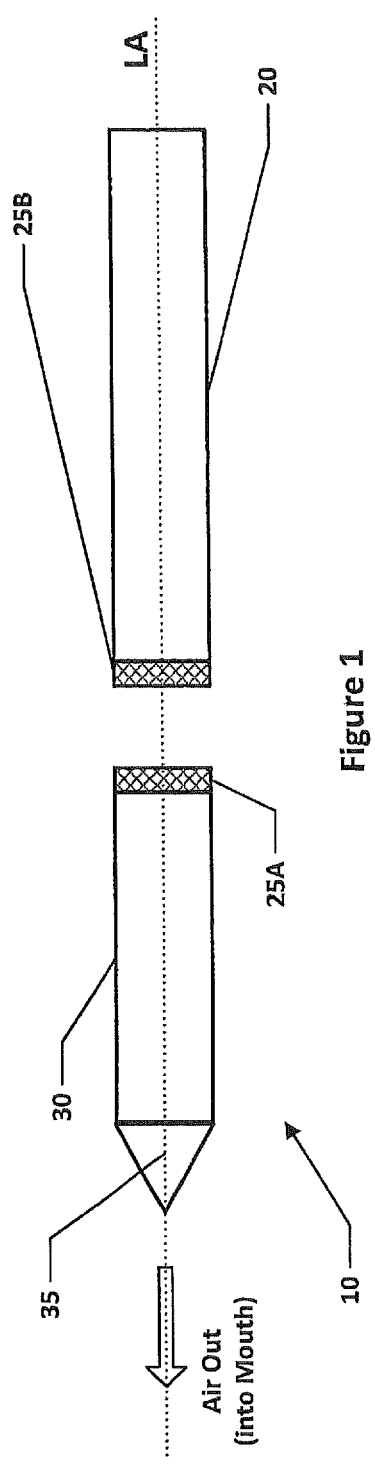

(51) Int. Cl.
  *A24F 40/46* (2020.01)
  *A61M 11/04* (2006.01)
  *A61M 15/06* (2006.01)
  *A24F 40/10* (2020.01)

(52) U.S. Cl.
  CPC ...... *A24F 40/10* (2020.01); *A61M 2205/0211* (2013.01); *A61M 2205/3341* (2013.01); *A61M 2205/3368* (2013.01)

(58) Field of Classification Search
  CPC .. A61M 2205/3341; A61M 2205/0211; A61M 2205/3368
  See application file for complete search history.

(56) References Cited

U.S. PATENT DOCUMENTS

| | | | |
|---|---|---|---|
| 576,653 | A | 2/1897 | Bowlby |
| 595,070 | A | 12/1897 | Oldenbusch |
| 744,074 | A | 11/1903 | Hiering |
| 799,844 | A | 9/1905 | Fuller |
| 885,374 | A | 4/1908 | Pohlig |
| 1,163,183 | A | 12/1915 | Stoll |
| D53,386 | S | 5/1919 | Thomas |
| 1,436,157 | A | 11/1922 | Fazio |
| 1,807,936 | A | 6/1931 | Saunders |
| 1,815,069 | A | 7/1931 | Petro |
| 1,937,120 | A | 11/1933 | Julius |
| 1,937,987 | A | 12/1933 | Sexton |
| 2,057,353 | A | 10/1936 | Whittmore, Jr. |
| 2,262,318 | A | 11/1941 | Fox |
| 2,371,006 | A | 3/1945 | Weaver |
| 2,411,946 | A | 12/1946 | Max |
| 2,467,923 | A | 4/1949 | Allen |
| 2,483,304 | A | 9/1949 | Rudolf |
| 2,522,952 | A | 9/1950 | Joseph |
| 2,658,368 | A | 11/1953 | Siegel |
| 2,782,910 | A | 2/1957 | Saul |
| 2,809,634 | A | 10/1957 | Hirotada |
| 3,080,624 | A | 3/1963 | Weber, III |
| 3,111,396 | A | 11/1963 | Ball |
| 3,165,225 | A | 1/1965 | Georg |
| 3,221,752 | A | 12/1965 | Strahm |
| 3,402,724 | A | 9/1968 | Blount et al. |
| 3,431,393 | A | 3/1969 | Katsuda |
| 3,433,632 | A | 3/1969 | Elbert et al. |
| 3,490,718 | A | 1/1970 | Vary |
| 3,496,336 | A | 2/1970 | Hingorany et al. |
| 3,521,643 | A | 7/1970 | Toth |
| 3,604,428 | A | 9/1971 | Moukaddem |
| 3,722,742 | A | 3/1973 | Wertz |
| 3,743,136 | A | 7/1973 | Chambers |
| 3,804,100 | A | 4/1974 | Fariello |
| 3,861,523 | A | 1/1975 | Fountain et al. |
| 3,863,803 | A | 2/1975 | Valcic |
| 3,915,145 | A | 10/1975 | Tomita |
| 3,964,902 | A | 6/1976 | Fletcher et al. |
| 4,009,713 | A | 3/1977 | Simmons et al. |
| 4,031,906 | A | 6/1977 | Knapp |
| 4,094,119 | A | 6/1978 | Sullivan |
| 4,117,850 | A | 10/1978 | Wood |
| 4,145,001 | A | 3/1979 | Weyenberg et al. |
| 4,161,283 | A | 7/1979 | Hyman |
| 4,190,412 | A | 2/1980 | Nitta |
| 4,193,513 | A | 3/1980 | Bull |
| 4,214,658 | A | 7/1980 | Crow |
| 4,253,476 | A | 3/1981 | Sato |
| 4,449,039 | A | 5/1984 | Fukazawa et al. |
| 4,503,851 | A | 3/1985 | Braunroth |
| D279,508 | S | 7/1985 | Shaak et al. |
| 4,579,858 | A | 4/1986 | Leo |
| 4,588,976 | A | 5/1986 | Jaselli |
| 4,597,961 | A | 7/1986 | Etscorn |
| 4,655,231 | A | 4/1987 | Ray |
| 4,676,237 | A | 6/1987 | Wood et al. |
| 4,677,992 | A | 7/1987 | Bliznak |
| 4,733,794 | A | 3/1988 | Kent |
| 4,735,217 | A | 4/1988 | Gerth et al. |
| 4,736,755 | A | 4/1988 | Oldham et al. |
| 4,753,383 | A | 6/1988 | Focke et al. |
| 4,793,478 | A | 12/1988 | Tudor |
| 4,830,028 | A | 5/1989 | Lawson |
| 4,848,374 | A | 7/1989 | Chard et al. |
| 4,858,630 | A | 8/1989 | Banerjee et al. |
| 4,878,832 | A | 11/1989 | Lynch |
| 4,885,129 | A | 12/1989 | Leonard et al. |
| 4,917,301 | A | 4/1990 | Munteanu |
| 4,922,901 | A | 5/1990 | Brooks et al. |
| 4,923,052 | A | 5/1990 | Englebert |
| 4,923,059 | A | 5/1990 | Evers et al. |
| 4,924,888 | A | 5/1990 | Perfetti |
| 4,947,874 | A | 8/1990 | Brooks et al. |
| 4,947,875 | A | 8/1990 | Brooks et al. |
| 4,961,438 | A | 10/1990 | Korte |
| 4,978,814 | A | 12/1990 | Honour |
| 5,027,837 | A | 7/1991 | Clearman et al. |
| 5,031,646 | A | 7/1991 | Lippiello |
| 5,044,550 | A | 9/1991 | Lamm |
| 5,046,514 | A | 9/1991 | Bolt |
| 5,060,671 | A | 10/1991 | Counts et al. |
| D322,687 | S | 12/1991 | Tschudin |
| 5,095,647 | A | 3/1992 | Zobele et al. |
| 5,095,921 | A | 3/1992 | Losee et al. |
| 5,096,921 | A | 3/1992 | Bollinger et al. |
| 5,099,861 | A | 3/1992 | Clearman et al. |
| 5,121,881 | A | 6/1992 | Lembeck |
| 5,167,242 | A | 12/1992 | Turner et al. |
| 5,179,966 | A | 1/1993 | Losee et al. |
| 5,234,008 | A | 8/1993 | Fagg |
| 5,247,947 | A | 9/1993 | Clearman et al. |
| 5,269,327 | A | 12/1993 | Counts et al. |
| D346,878 | S | 5/1994 | Utsch et al. |
| 5,322,075 | A | 6/1994 | Deevi et al. |
| 5,357,271 | A | 10/1994 | Wiklof et al. |
| 5,388,574 | A | 2/1995 | Ingebrethsen |
| 5,390,864 | A | 2/1995 | Alexander |
| 5,404,890 | A | 4/1995 | Gentry et al. |
| 5,408,574 | A | 4/1995 | Deevi et al. |
| 5,448,317 | A | 9/1995 | Huang |
| 5,479,948 | A | 1/1996 | Counts et al. |
| 5,497,792 | A | 3/1996 | Prasad et al. |
| 5,501,236 | A | 3/1996 | Hill et al. |
| 5,505,214 | A | 4/1996 | Collins et al. |
| 5,530,225 | A | 6/1996 | Hajaligol |
| 5,540,241 | A | 7/1996 | Kim |
| 5,553,791 | A | 9/1996 | Alexander |
| 5,568,819 | A | 10/1996 | Gentry et al. |
| 5,626,866 | A | 5/1997 | Ebert et al. |
| 5,636,787 | A | 6/1997 | Gowhari |
| 5,649,554 | A | 7/1997 | Sprinkel et al. |
| 5,659,656 | A | 8/1997 | Das |
| 5,666,977 | A | 9/1997 | Higgins et al. |
| 5,692,291 | A | 12/1997 | Deevi et al. |
| D392,069 | S | 3/1998 | Rowland |
| 5,743,251 | A | 4/1998 | Howell et al. |
| D404,201 | S | 1/1999 | Wennerstrom |
| 5,865,185 | A | 2/1999 | Collins et al. |
| 5,875,968 | A | 3/1999 | Miller et al. |
| 5,878,722 | A | 3/1999 | Gras et al. |
| 5,878,752 | A | 3/1999 | Adams et al. |
| 5,894,841 | A | 4/1999 | Voges |
| 5,896,984 | A | 4/1999 | Focke et al. |
| D414,892 | S | 10/1999 | Chen |
| 5,967,312 | A | 10/1999 | Jacobs |
| 6,040,560 | A | 3/2000 | Fleischhauer et al. |
| 6,058,711 | A | 5/2000 | Maciaszek et al. |
| 6,065,592 | A | 5/2000 | Wik |
| 6,095,505 | A | 8/2000 | Miller |
| 6,119,684 | A | 9/2000 | Noehl et al. |
| D432,263 | S | 10/2000 | Issa |
| D434,217 | S | 11/2000 | Packard et al. |
| D434,979 | S | 12/2000 | Liu |
| 6,155,268 | A | 12/2000 | Takeuchi |
| D436,725 | S | 1/2001 | Rogers |

(56) References Cited

U.S. PATENT DOCUMENTS

| | | |
|---|---|---|
| D438,003 S | 2/2001 | Minagawa et al. |
| D441,133 S | 4/2001 | Emery |
| 6,275,650 B1 | 8/2001 | Lambert |
| D449,521 S | 10/2001 | Pinkus et al. |
| 6,321,757 B1 | 11/2001 | McCutcheon |
| 6,446,793 B1 | 9/2002 | Layshock |
| D466,012 S | 11/2002 | Baker |
| D470,765 S | 2/2003 | Baker |
| D471,804 S | 3/2003 | Staples |
| D472,012 S | 3/2003 | South |
| 6,527,166 B1 | 3/2003 | Focke et al. |
| 6,530,495 B1 | 3/2003 | Joseph |
| 6,561,391 B1 | 5/2003 | Baker |
| 6,652,804 B1 | 11/2003 | Neumann et al. |
| 6,681,998 B2 | 1/2004 | Sharpe et al. |
| 6,701,921 B2 | 3/2004 | Sprinkel et al. |
| 6,715,605 B1 | 4/2004 | Manservigi et al. |
| D493,617 S | 8/2004 | Armato |
| 6,790,496 B1 | 9/2004 | Levander et al. |
| 6,799,576 B2 | 10/2004 | Farr |
| 6,830,046 B2 | 12/2004 | Blakley et al. |
| D509,732 S | 9/2005 | Staples |
| 7,100,618 B2 | 9/2006 | Dominguez |
| 7,112,712 B1 | 9/2006 | Ancell |
| D545,186 S | 6/2007 | Liebe et al. |
| D549,573 S | 8/2007 | Liebe et al. |
| 7,253,282 B2 | 8/2007 | Dehmlow et al. |
| 7,263,228 B2 | 8/2007 | Mori |
| 7,263,282 B2 | 8/2007 | Meyer |
| D550,455 S | 9/2007 | Barnhart |
| D566,329 S | 4/2008 | Bagaric et al. |
| D566,890 S | 4/2008 | Bagaric et al. |
| 7,389,878 B1 | 6/2008 | Torrico |
| D573,889 S | 7/2008 | Short et al. |
| 7,400,940 B2 | 7/2008 | McRae et al. |
| D575,451 S | 8/2008 | Jones et al. |
| 7,455,176 B2 | 11/2008 | Focke et al. |
| 7,540,286 B2 | 6/2009 | Cross et al. |
| 7,565,969 B2 | 7/2009 | He |
| 7,575,002 B2 | 8/2009 | Demars et al. |
| D606,854 S | 12/2009 | Greenhalgh |
| D610,983 S | 3/2010 | Wai |
| D611,806 S | 3/2010 | Bried |
| D613,903 S | 4/2010 | Wu |
| D613,904 S | 4/2010 | Wu |
| D616,753 S | 6/2010 | Beam et al. |
| 7,726,320 B2 | 6/2010 | Robinson et al. |
| 7,767,698 B2 | 8/2010 | Warchol et al. |
| 7,832,410 B2 | 11/2010 | Hon |
| D628,469 S | 12/2010 | Taylor et al. |
| D631,838 S | 2/2011 | Cheng |
| D636,257 S | 4/2011 | Bougoulas et al. |
| 7,992,554 B2 | 8/2011 | Radomski et al. |
| D649,658 S | 11/2011 | Belfance et al. |
| D650,738 S | 12/2011 | Leung |
| 8,079,371 B2 | 12/2011 | Robinson et al. |
| 8,113,343 B2 | 2/2012 | Aakerlind |
| D656,094 S | 3/2012 | Wu |
| 8,156,944 B2 | 4/2012 | Han |
| D661,016 S | 5/2012 | Borges et al. |
| D671,677 S | 11/2012 | Wu |
| D671,678 S | 11/2012 | Wu |
| 8,307,834 B1 | 11/2012 | Palmerino et al. |
| D672,642 S | 12/2012 | Supranowicz |
| D674,539 S | 1/2013 | Wu |
| 8,365,742 B2 | 2/2013 | Hon |
| 8,375,957 B2 | 2/2013 | Hon |
| 8,393,331 B2 | 3/2013 | Hon |
| 8,430,106 B2 | 4/2013 | Potter et al. |
| 8,448,783 B2 | 5/2013 | Vecchi |
| 8,490,628 B2 | 7/2013 | Hon |
| 8,511,318 B2 | 8/2013 | Hon |
| D693,055 S | 11/2013 | Manca et al. |
| D700,397 S | 2/2014 | Manca et al. |
| 8,689,805 B2 | 4/2014 | Hon |
| 8,752,545 B2 | 6/2014 | Buchberger |
| 8,794,245 B1 | 8/2014 | Scatterday |
| 8,833,364 B2 | 9/2014 | Buchberger |
| D715,760 S | 10/2014 | Kim et al. |
| D716,267 S | 10/2014 | Kim et al. |
| 8,869,793 B1 | 10/2014 | Spandorfer et al. |
| 8,910,640 B2 | 12/2014 | Sears et al. |
| D720,884 S | 1/2015 | Liu |
| 8,948,578 B2 | 2/2015 | Buchberger |
| D723,738 S | 3/2015 | Liu |
| 8,967,155 B2 | 3/2015 | Bundren et al. |
| 8,997,753 B2 | 4/2015 | Li et al. |
| 9,055,617 B2 | 6/2015 | Thorens et al. |
| D736,460 S | 8/2015 | McKeon et al. |
| D737,507 S | 8/2015 | Liu |
| 9,215,895 B2 * | 12/2015 | Bowen ............... A24B 15/16 |
| 9,609,894 B2 | 4/2017 | Abramov et al. |
| 9,623,205 B2 | 4/2017 | Buchberger |
| 9,730,276 B2 | 8/2017 | Vissa et al. |
| 9,943,108 B2 | 4/2018 | Lord |
| 9,961,939 B2 | 5/2018 | Reevell |
| 9,974,335 B2 | 5/2018 | Lord |
| 9,974,743 B2 | 5/2018 | Rose et al. |
| 9,986,760 B2 | 6/2018 | Macko et al. |
| 10,010,695 B2 | 7/2018 | Buchberger |
| 10,045,562 B2 | 8/2018 | Buchberger |
| 10,278,421 B2 | 5/2019 | Lord |
| 10,368,582 B2 | 8/2019 | Lord |
| 10,765,147 B2 | 9/2020 | Buchberger et al. |
| 11,044,937 B2 | 6/2021 | McAdam |
| 2001/0004934 A1 | 6/2001 | Yamamoto et al. |
| 2001/0042546 A1 | 11/2001 | Umeda et al. |
| 2002/0005207 A1 | 1/2002 | Wrenn et al. |
| 2002/0016370 A1 | 2/2002 | Shytle et al. |
| 2002/0059939 A1 | 5/2002 | Fox |
| 2002/0079309 A1 | 6/2002 | Cox et al. |
| 2003/0005620 A1 | 1/2003 | Ananth et al. |
| 2003/0049025 A1 | 3/2003 | Neumann et al. |
| 2003/0056791 A1 | 3/2003 | Nichols et al. |
| 2003/0064340 A1 | 4/2003 | Pappas |
| 2003/0079309 A1 | 5/2003 | Vandenbelt et al. |
| 2003/0106551 A1 | 6/2003 | Sprinkel et al. |
| 2003/0106552 A1 | 6/2003 | Sprinkel et al. |
| 2003/0108342 A1 | 6/2003 | Sherwood et al. |
| 2003/0108743 A1 | 6/2003 | Anderson |
| 2003/0136399 A1 | 7/2003 | Foley et al. |
| 2003/0136404 A1 | 7/2003 | Hindle et al. |
| 2003/0168057 A1 | 9/2003 | Snyder et al. |
| 2003/0176467 A1 | 9/2003 | Andersson |
| 2003/0192540 A1 | 10/2003 | Myrman |
| 2003/0200964 A1 | 10/2003 | Blakley et al. |
| 2003/0202169 A1 | 10/2003 | Liu |
| 2004/0025865 A1 | 2/2004 | Nichols et al. |
| 2004/0031485 A1 | 2/2004 | Rustad et al. |
| 2004/0056651 A1 | 3/2004 | Marietta |
| 2004/0081624 A1 | 4/2004 | Nguyen et al. |
| 2004/0129793 A1 | 7/2004 | Nguyen et al. |
| 2004/0198818 A1 | 10/2004 | Quallich et al. |
| 2004/0210151 A1 | 10/2004 | Tsukashima et al. |
| 2004/0213744 A1 | 10/2004 | Lulla |
| 2004/0223917 A1 | 11/2004 | Hindle et al. |
| 2004/0226568 A1 | 11/2004 | Takeuchi et al. |
| 2004/0255941 A1 | 12/2004 | Nichols et al. |
| 2004/0261487 A1 | 12/2004 | Chen |
| 2005/0009870 A1 | 1/2005 | Sher |
| 2005/0016550 A1 | 1/2005 | Katase |
| 2005/0063686 A1 | 3/2005 | Whittle et al. |
| 2005/0087460 A1 | 4/2005 | Bruhn et al. |
| 2005/0133049 A1 | 6/2005 | Fournier et al. |
| 2005/0145260 A1 | 7/2005 | Inagaki et al. |
| 2005/0155985 A1 | 7/2005 | Meyer |
| 2005/0194013 A1 | 9/2005 | Wright |
| 2005/0204799 A1 | 9/2005 | Koch |
| 2005/0211243 A1 | 9/2005 | Esser |
| 2005/0224375 A1 | 10/2005 | Focke et al. |
| 2005/0235991 A1 | 10/2005 | Nichols et al. |
| 2005/0247436 A1 | 11/2005 | Hsu |
| 2005/0268911 A1 | 12/2005 | Cross et al. |
| 2006/0018840 A1 | 1/2006 | Lechuga-Ballesferos |

(56) References Cited

U.S. PATENT DOCUMENTS

| | | |
|---|---|---|
| 2006/0073182 A1 | 4/2006 | Wong |
| 2006/0078477 A1 | 4/2006 | Althouse et al. |
| 2006/0095311 A1 | 5/2006 | Thompson |
| 2006/0137681 A1 | 6/2006 | Von et al. |
| 2006/0180143 A1 | 8/2006 | Lind et al. |
| 2006/0196518 A1 | 9/2006 | Hon |
| 2006/0283468 A1 | 12/2006 | Lipowicz |
| 2007/0014549 A1 | 1/2007 | Demarest et al. |
| 2007/0045288 A1 | 3/2007 | Nelson |
| 2007/0062548 A1 | 3/2007 | Horstmann et al. |
| 2007/0074722 A1 | 4/2007 | Giroux et al. |
| 2007/0076067 A1 | 4/2007 | Hamano et al. |
| 2007/0082038 A1 | 4/2007 | Gale et al. |
| 2007/0102013 A1 | 5/2007 | Adams et al. |
| 2007/0107879 A1 | 5/2007 | Radomski et al. |
| 2007/0134169 A1 | 6/2007 | Rabinoff |
| 2007/0135461 A1 | 6/2007 | Rodgers |
| 2007/0144514 A1 | 6/2007 | Yeates et al. |
| 2007/0155255 A1 | 7/2007 | Galauner et al. |
| 2007/0193895 A1 | 8/2007 | Weiss et al. |
| 2007/0267031 A1 | 11/2007 | Hon |
| 2007/0267032 A1 | 11/2007 | Shan |
| 2007/0280972 A1 | 12/2007 | Zhang |
| 2008/0017204 A1 | 1/2008 | Braunshteyn et al. |
| 2008/0092912 A1 | 4/2008 | Robinson |
| 2008/0138423 A1 | 6/2008 | Gonda |
| 2008/0149118 A1 | 6/2008 | Oglesby et al. |
| 2008/0156326 A1 | 7/2008 | Belcastro et al. |
| 2008/0216828 A1 | 9/2008 | Wensley et al. |
| 2008/0223382 A1 | 9/2008 | Zeanah |
| 2008/0228214 A1 | 9/2008 | Hoan et al. |
| 2008/0241255 A1 | 10/2008 | Rose et al. |
| 2008/0302375 A1 | 12/2008 | Andersson et al. |
| 2009/0009534 A1 | 1/2009 | Perani et al. |
| 2009/0023819 A1 | 1/2009 | Axelsson |
| 2009/0050139 A1 | 2/2009 | Watanabe et al. |
| 2009/0090472 A1 | 4/2009 | Radomski |
| 2009/0095311 A1 | 4/2009 | Han |
| 2009/0095312 A1 | 4/2009 | Herbrich et al. |
| 2009/0133691 A1 | 5/2009 | Yamada et al. |
| 2009/0188490 A1 | 7/2009 | Han |
| 2009/0220222 A1 | 9/2009 | Rabin et al. |
| 2009/0241947 A1 | 10/2009 | Bedini et al. |
| 2009/0266837 A1 | 10/2009 | Gelardi et al. |
| 2009/0272379 A1 | 11/2009 | Thorens et al. |
| 2009/0288966 A1 | 11/2009 | Minarelli et al. |
| 2009/0293892 A1 | 12/2009 | Williams et al. |
| 2009/0324206 A1 | 12/2009 | Young et al. |
| 2010/0003904 A1 | 1/2010 | Duescher |
| 2010/0006113 A1 | 1/2010 | Urtsev et al. |
| 2010/0039066 A1 | 2/2010 | Yuan et al. |
| 2010/0059070 A1 | 3/2010 | Potter et al. |
| 2010/0065653 A1 | 3/2010 | Wingo et al. |
| 2010/0083959 A1 | 4/2010 | Siller |
| 2010/0108059 A1 | 5/2010 | Axelsson et al. |
| 2010/0116691 A1 | 5/2010 | Papadimitrakopoulos |
| 2010/0181387 A1 | 7/2010 | Zaffaroni et al. |
| 2010/0182608 A1 | 7/2010 | Zribi et al. |
| 2010/0200006 A1 | 8/2010 | Robinson et al. |
| 2010/0211011 A1 | 8/2010 | Haar |
| 2010/0236546 A1 | 9/2010 | Yamada et al. |
| 2010/0242974 A1 | 9/2010 | Pan |
| 2010/0260688 A1 | 10/2010 | Warchol |
| 2010/0313901 A1 | 12/2010 | Stahle et al. |
| 2011/0011396 A1 | 1/2011 | Fang |
| 2011/0036363 A1 | 2/2011 | Urtsev et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0180433 A1 | 7/2011 | Rennecamp |
| 2011/0192914 A1 | 8/2011 | Ishigami |
| 2011/0209717 A1 | 9/2011 | Han |
| 2011/0226236 A1 | 9/2011 | Buchberger |
| 2011/0268809 A1 | 11/2011 | Brinkley |
| 2011/0274628 A1 | 11/2011 | Borschke |
| 2011/0277757 A1 | 11/2011 | Terry et al. |
| 2011/0278189 A1 | 11/2011 | Terry et al. |
| 2011/0290267 A1 | 12/2011 | Yamada et al. |
| 2011/0297166 A1 | 12/2011 | Takeuchi et al. |
| 2011/0303231 A1 | 12/2011 | Li et al. |
| 2011/0309157 A1 | 12/2011 | Yang et al. |
| 2012/0111347 A1 | 5/2012 | Hon |
| 2012/0145169 A1 | 6/2012 | Wu |
| 2012/0180994 A1 | 7/2012 | Yang et al. |
| 2012/0180995 A1 | 7/2012 | Yang et al. |
| 2012/0199146 A1 | 8/2012 | Marangos |
| 2012/0227752 A1 | 9/2012 | Alelov |
| 2012/0227753 A1 | 9/2012 | Newton |
| 2012/0242974 A1 | 9/2012 | Lavalley et al. |
| 2012/0255567 A1 | 10/2012 | Rose et al. |
| 2012/0260927 A1 | 10/2012 | Liu |
| 2012/0285476 A1 | 11/2012 | Hon |
| 2013/0074857 A1 | 3/2013 | Buchberger |
| 2013/0081623 A1 | 4/2013 | Buchberg |
| 2013/0081642 A1 | 4/2013 | Safari |
| 2013/0087160 A1 | 4/2013 | Gherghe |
| 2013/0098786 A1 | 4/2013 | Collins |
| 2013/0112214 A1 | 5/2013 | Bundren et al. |
| 2013/0142782 A1 | 6/2013 | Rahmel et al. |
| 2013/0192615 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192623 A1 | 8/2013 | Tucker et al. |
| 2013/0213419 A1 | 8/2013 | Tucker et al. |
| 2013/0228191 A1 | 9/2013 | Newton |
| 2013/0255702 A1 | 10/2013 | Griffith, Jr. et al. |
| 2013/0284192 A1 | 10/2013 | Peleg et al. |
| 2013/0298905 A1 | 11/2013 | Levin |
| 2013/0306084 A1 | 11/2013 | Flick |
| 2013/0319407 A1 | 12/2013 | Liu |
| 2013/0319435 A1 | 12/2013 | Flick |
| 2013/0333700 A1 | 12/2013 | Buchberger |
| 2013/0340779 A1 | 12/2013 | Liu |
| 2013/0341218 A1 | 12/2013 | Liu |
| 2013/0342157 A1 | 12/2013 | Liu |
| 2014/0000638 A1 | 1/2014 | Sebastian et al. |
| 2014/0007863 A1 | 1/2014 | Chen |
| 2014/0007892 A1 | 1/2014 | Liu |
| 2014/0018840 A1 | 1/2014 | Morgan |
| 2014/0020697 A1 | 1/2014 | Liu |
| 2014/0023824 A1 | 1/2014 | Masanek et al. |
| 2014/0048086 A1 | 2/2014 | Zhanghua |
| 2014/0053831 A1 | 2/2014 | Leamon et al. |
| 2014/0060528 A1 | 3/2014 | Liu |
| 2014/0060554 A1 | 3/2014 | Collett |
| 2014/0060555 A1 | 3/2014 | Chang et al. |
| 2014/0064715 A1 | 3/2014 | Greim et al. |
| 2014/0106155 A1 | 4/2014 | Espinosa |
| 2014/0123989 A1 | 5/2014 | Lamothe |
| 2014/0166027 A1 | 6/2014 | Fuisz |
| 2014/0182608 A1 | 7/2014 | Egoyants et al. |
| 2014/0196717 A1 | 7/2014 | Liu |
| 2014/0196731 A1 | 7/2014 | Scatterday |
| 2014/0202454 A1 | 7/2014 | Buchberger |
| 2014/0202476 A1 | 7/2014 | Egoyants et al. |
| 2014/0209105 A1 | 7/2014 | Sears et al. |
| 2014/0216485 A1 | 8/2014 | Egoyants et al. |
| 2014/0238396 A1 | 8/2014 | Buchberger |
| 2014/0238422 A1 | 8/2014 | Plunkett et al. |
| 2014/0238423 A1 | 8/2014 | Tucker et al. |
| 2014/0238424 A1 | 8/2014 | Macko et al. |
| 2014/0253144 A1 | 9/2014 | Novak |
| 2014/0261486 A1 | 9/2014 | Potter et al. |
| 2014/0261487 A1 | 9/2014 | Chapman |
| 2014/0261488 A1 | 9/2014 | Tucker |
| 2014/0261489 A1 | 9/2014 | Cadieux |
| 2014/0261490 A1 | 9/2014 | Kane |
| 2014/0261493 A1 | 9/2014 | Smith |
| 2014/0261495 A1 | 9/2014 | Novak et al. |
| 2014/0270726 A1 | 9/2014 | Egoyants et al. |
| 2014/0270729 A1 | 9/2014 | Depiano et al. |

(56) References Cited

U.S. PATENT DOCUMENTS

| | | |
|---|---|---|
| 2014/0270730 A1 | 9/2014 | Depiano et al. |
| 2014/0283825 A1 | 9/2014 | Buchberger |
| 2014/0286630 A1 | 9/2014 | Buchberger |
| 2014/0299125 A1 | 10/2014 | Buchberger |
| 2014/0299141 A1 | 10/2014 | Flick |
| 2014/0305431 A1 | 10/2014 | Holley et al. |
| 2014/0332019 A1 | 11/2014 | Liu |
| 2014/0338680 A1 | 11/2014 | Abramov et al. |
| 2014/0345635 A1 | 11/2014 | Rabinowitz |
| 2015/0020823 A1 | 1/2015 | Lipowciz |
| 2015/0101626 A1 | 4/2015 | Li et al. |
| 2015/0114411 A1 | 4/2015 | Buchberger |
| 2015/0128964 A1 | 5/2015 | Bundren et al. |
| 2015/0128971 A1 | 5/2015 | Verleur et al. |
| 2015/0136756 A1 | 5/2015 | Vissa et al. |
| 2015/0157055 A1 | 6/2015 | Lord |
| 2015/0164143 A1 | 6/2015 | Maas |
| 2015/0181934 A1 | 7/2015 | Lyubomirskiy et al. |
| 2015/0181937 A1 | 7/2015 | Dubief et al. |
| 2015/0196058 A1 | 7/2015 | Lord |
| 2015/0201675 A1 | 7/2015 | Lord |
| 2015/0208728 A1 | 7/2015 | Lord |
| 2015/0250232 A1 | 9/2015 | Hon |
| 2015/0313275 A1 | 11/2015 | Anderson |
| 2016/0021934 A1 | 1/2016 | Cadieux et al. |
| 2016/0073693 A1 | 3/2016 | Reevell |
| 2016/0101909 A1 | 4/2016 | Schennum et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0150825 A1 | 6/2016 | Mironov et al. |
| 2016/0278163 A1 | 9/2016 | Chen |
| 2016/0353804 A1 | 12/2016 | Lord |
| 2017/0006916 A1 | 1/2017 | Liu |
| 2017/0027225 A1 | 2/2017 | Buchberger et al. |
| 2017/0042245 A1 | 2/2017 | Buchberger et al. |
| 2017/0135401 A1* | 5/2017 | Dickens ................ A24F 40/50 |
| 2017/0143038 A1* | 5/2017 | Dickens ................ A61M 15/06 |
| 2017/0188629 A1 | 7/2017 | Dickens et al. |
| 2017/0188630 A1 | 7/2017 | Buchberger |
| 2017/0197043 A1 | 7/2017 | Buchberger |
| 2017/0197044 A1 | 7/2017 | Buchberger |
| 2017/0197046 A1 | 7/2017 | Buchberger |
| 2017/0215476 A1* | 8/2017 | Dickens ................ A24B 15/167 |
| 2017/0224014 A1* | 8/2017 | Fraser ................... A24F 40/485 |
| 2017/0231284 A1* | 8/2017 | Newns ................... A24F 40/50 |
| | | 131/328 |
| 2017/0251725 A1* | 9/2017 | Buchberger ............ A24F 40/53 |
| 2018/0192705 A1 | 7/2018 | Lord |
| 2018/0235284 A1 | 8/2018 | Lord |
| 2019/0254350 A1 | 8/2019 | Lord |
| 2019/0289920 A1 | 9/2019 | Lord |
| 2021/0146067 A1 | 5/2021 | Buchberger |
| 2021/0196919 A1 | 7/2021 | Potharaju et al. |

FOREIGN PATENT DOCUMENTS

| | | |
|---|---|---|
| AT | 507188 A4 | 3/2010 |
| AT | 508244 A4 | 12/2010 |
| AT | 510405 A4 | 4/2012 |
| AT | 510504 A1 | 4/2012 |
| AU | 6391373 A | 6/1975 |
| AU | 6393173 A | 6/1975 |
| AU | 2015341516 B2 | 12/2017 |
| AU | 2015341517 B2 | 1/2018 |
| AU | 2015255045 B2 | 3/2018 |
| AU | 2015359102 B2 | 6/2018 |
| AU | 2017256084 B2 | 9/2020 |
| BR | 6402132 U | 7/1986 |
| BR | 112017009252 A2 | 1/2018 |
| CA | 2446102 | 4/2000 |
| CA | 2309376 A1 | 11/2000 |
| CA | 2824970 A1 | 8/2012 |
| CA | 2909967 A1 | 11/2014 |
| CH | 698603 B1 | 9/2009 |
| CL | 199400288 A1 | 8/1995 |
| CL | 199900377 | 7/1999 |
| CL | 2004000365 A1 | 2/2005 |
| CL | 2012000958 A1 | 1/2013 |
| CL | 2013002357 A1 | 11/2013 |
| CL | 2017001108 A1 | 1/2018 |
| CL | 2017001137 A1 | 1/2018 |
| CN | 86103434 A | 11/1986 |
| CN | 1039530 A | 2/1990 |
| CN | 2092880 U | 1/1992 |
| CN | 1102647 A | 5/1995 |
| CN | 2220168 Y | 2/1996 |
| CN | 1126425 A | 7/1996 |
| CN | 1205849 A | 1/1999 |
| CN | 1312730 A | 9/2001 |
| CN | 1329567 A | 1/2002 |
| CN | 1333657 A | 1/2002 |
| CN | 1337903 A | 2/2002 |
| CN | 2485265 Y | 4/2002 |
| CN | 1530041 A | 9/2004 |
| CN | 2660914 Y | 12/2004 |
| CN | 1607911 A | 4/2005 |
| CN | 1607950 A | 4/2005 |
| CN | 2719043 Y | 8/2005 |
| CN | 1694765 A | 11/2005 |
| CN | 1703279 A | 11/2005 |
| CN | 2754386 Y | 2/2006 |
| CN | 2777995 Y | 5/2006 |
| CN | 1286409 C | 11/2006 |
| CN | 2904674 Y | 5/2007 |
| CN | 200966824 Y | 10/2007 |
| CN | 101115901 A | 1/2008 |
| CN | 201023852 Y | 2/2008 |
| CN | 201067079 Y | 6/2008 |
| CN | 201079011 Y | 7/2008 |
| CN | 101437496 A | 5/2009 |
| CN | 201238609 Y | 5/2009 |
| CN | 201240612 Y | 5/2009 |
| CN | 101557728 A | 10/2009 |
| CN | 201375023 Y | 1/2010 |
| CN | 101648041 A | 2/2010 |
| CN | 201430913 Y | 3/2010 |
| CN | 101843368 A | 9/2010 |
| CN | 201592850 U | 9/2010 |
| CN | 101878958 A | 11/2010 |
| CN | 101925309 A | 12/2010 |
| CN | 201657770 U | 12/2010 |
| CN | 101951796 A | 1/2011 |
| CN | 102014677 A | 4/2011 |
| CN | 201830900 U | 5/2011 |
| CN | 201860753 U | 6/2011 |
| CN | 102264249 A | 11/2011 |
| CN | 102264420 A | 11/2011 |
| CN | 102326869 A | 1/2012 |
| CN | 202122096 U | 1/2012 |
| CN | 102389166 A | 3/2012 |
| CN | 202172846 U | 3/2012 |
| CN | 102655773 A | 9/2012 |
| CN | 102753047 A | 10/2012 |
| CN | 102883766 A | 1/2013 |
| CN | 202722498 U | 2/2013 |
| CN | 202750708 U | 2/2013 |
| CN | 103052380 A | 4/2013 |
| CN | 204317492 U | 5/2013 |
| CN | 103338664 A | 10/2013 |
| CN | 103491958 A | 1/2014 |
| CN | 103960782 A | 8/2014 |
| CN | 203986095 U | 12/2014 |
| CN | 204048047 U | 12/2014 |
| CN | 104602553 A | 5/2015 |
| CN | 104684422 A | 6/2015 |
| CN | 204598339 U | 8/2015 |
| CN | 104983079 A | 10/2015 |
| CN | 105310114 A | 2/2016 |
| CN | 105394816 A | 3/2016 |
| CN | 205106385 U | 3/2016 |
| CN | 106102863 A | 11/2016 |
| CN | 106998820 B | 10/2019 |

(56) References Cited

FOREIGN PATENT DOCUMENTS

| | | |
|---|---|---|
| DE | 594585 C | 3/1934 |
| DE | 1950439 A1 | 4/1971 |
| DE | 2653133 A1 | 5/1978 |
| DE | 2940797 A1 | 4/1981 |
| DE | 3148335 A1 | 7/1983 |
| DE | 3218760 A1 | 12/1983 |
| DE | 3936687 A1 | 5/1990 |
| DE | 29719509 U1 | 1/1998 |
| DE | 19630619 A1 | 2/1998 |
| DE | 19654945 A1 | 3/1998 |
| DE | 29803260 U1 | 7/1998 |
| DE | 10330681 B3 | 6/2004 |
| DE | 202006013439 U1 | 10/2006 |
| DE | 102006004484 A1 | 8/2007 |
| DE | 202013100606 U1 | 2/2013 |
| EA | 009116 B1 | 10/2007 |
| EA | 019736 B1 | 5/2014 |
| EA | 022685 B1 | 2/2016 |
| EA | 201692191 A1 | 3/2017 |
| EP | 0280262 A2 | 8/1988 |
| EP | 0283672 A2 | 9/1988 |
| EP | 0289342 A2 | 11/1988 |
| EP | 0290911 A2 | 11/1988 |
| EP | 0295122 A2 | 12/1988 |
| EP | 0358002 A2 | 3/1990 |
| EP | 0358114 A2 | 3/1990 |
| EP | 0444553 A2 | 9/1991 |
| EP | 0488488 A1 | 6/1992 |
| EP | 0520231 A2 | 12/1992 |
| EP | 0845220 A1 | 6/1998 |
| EP | 0847220 A2 | 6/1998 |
| EP | 0893071 A1 | 1/1999 |
| EP | 0893171 A1 | 1/1999 |
| EP | 1166814 A2 | 1/2002 |
| EP | 1166847 A2 | 1/2002 |
| EP | 1468618 A1 | 10/2004 |
| EP | 1 509 227 | 3/2005 |
| EP | 1618803 | 1/2006 |
| EP | 1736065 A1 | 12/2006 |
| EP | 1757921 A2 | 2/2007 |
| EP | 1772166 A1 | 4/2007 |
| EP | 1772199 A1 | 4/2007 |
| EP | 1820748 A1 | 8/2007 |
| EP | 1847671 A1 | 10/2007 |
| EP | 1950439 A1 | 7/2008 |
| EP | 2018886 A1 | 1/2009 |
| EP | 2022349 A1 | 2/2009 |
| EP | 2022350 A1 | 2/2009 |
| EP | 1509227 B1 | 10/2009 |
| EP | 2113178 A1 | 11/2009 |
| EP | 2234891 A2 | 10/2010 |
| EP | 2340729 A1 | 7/2011 |
| EP | 2358223 A1 | 8/2011 |
| EP | 2358418 A1 | 8/2011 |
| EP | 2468116 A1 | 6/2012 |
| EP | 2468118 A1 | 6/2012 |
| EP | 2477607 A1 | 7/2012 |
| EP | 2404515 A1 | 11/2012 |
| EP | 2698070 A1 | 2/2014 |
| EP | 2762019 A1 | 8/2014 |
| EP | 2779786 A1 | 9/2014 |
| EP | 2785208 A1 | 10/2014 |
| EP | 2801273 A2 | 11/2014 |
| EP | 2835062 A1 | 2/2015 |
| EP | 2871985 A1 | 5/2015 |
| EP | 2907397 A1 | 8/2015 |
| EP | 2967144 A1 | 1/2016 |
| EP | 2993999 A1 | 3/2016 |
| EP | 3021699 A2 | 5/2016 |
| EP | 3073846 A2 | 10/2016 |
| EP | 3076805 A1 | 10/2016 |
| EP | 3145348 A1 | 3/2017 |
| EP | 2907397 B1 | 9/2017 |
| EP | 3284500 A1 | 2/2018 |
| EP | 3117860 B1 | 1/2019 |
| EP | 3214957 B1 | 2/2019 |
| EP | 3229621 B1 | 1/2020 |
| EP | 3491941 B1 | 8/2020 |
| EP | 3738632 B1 | 2/2022 |
| FR | 472030 A | 11/1914 |
| FR | 960469 A | 4/1950 |
| FR | 1292446 A | 5/1962 |
| GB | 190903566 A | 6/1909 |
| GB | 190930472 A | 12/1910 |
| GB | 191100628 A | 11/1911 |
| GB | 25575 | 3/1912 |
| GB | 191311086 A | 9/1913 |
| GB | 110216 A | 10/1917 |
| GB | 111454 A | 11/1917 |
| GB | 120016 A | 10/1918 |
| GB | 160493 A | 3/1921 |
| GB | 163124 A | 5/1921 |
| GB | 215992 A | 5/1924 |
| GB | 220229 A | 8/1924 |
| GB | 268967 A | 4/1927 |
| GB | 402064 A | 11/1933 |
| GB | 438750 A | 11/1935 |
| GB | 507955 A | 6/1939 |
| GB | 544329 A | 4/1942 |
| GB | 565574 A | 11/1944 |
| GB | 611596 A | 11/1948 |
| GB | 626888 A | 7/1949 |
| GB | 871869 A | 7/1961 |
| GB | 1046183 A | 10/1966 |
| GB | 1313525 A | 4/1973 |
| GB | 2 133 691 A | 8/1984 |
| GB | 2275464 A | 8/1994 |
| GB | 2068034 A | 11/1997 |
| GB | 2369108 A | 5/2002 |
| GB | 4000273 | 12/2006 |
| GB | 4006615 | 10/2008 |
| GB | 2504075 A | 1/2014 |
| GB | 2513635 A | 11/2014 |
| HK | 1196511 A1 | 12/2014 |
| HK | 1226611 A | 10/2017 |
| IE | S20060065 A2 | 10/2006 |
| IN | 0351/KOL/2006 | 7/2007 |
| JP | S5289386 A | 7/1977 |
| JP | S5752456 A | 3/1982 |
| JP | S57140354 A | 8/1982 |
| JP | S59106340 A | 6/1984 |
| JP | S59135878 A | 8/1984 |
| JP | S6121542 A | 1/1986 |
| JP | S6121542 B2 | 5/1986 |
| JP | S6196763 A | 5/1986 |
| JP | S6196765 A | 5/1986 |
| JP | H01104153 A | 4/1989 |
| JP | H01117775 A | 5/1989 |
| JP | H02124081 A | 5/1990 |
| JP | H02124082 A | 5/1990 |
| JP | H0548944 A | 2/1993 |
| JP | H05103836 A | 4/1993 |
| JP | H05309136 A | 11/1993 |
| JP | 3003543 U | 10/1994 |
| JP | H06303837 A | 11/1994 |
| JP | H06315366 A | 11/1994 |
| JP | H07147965 A | 6/1995 |
| JP | H08299862 A | 11/1996 |
| JP | H08511176 A | 11/1996 |
| JP | H1189551 A | 4/1999 |
| JP | H11503912 A | 4/1999 |
| JP | H11514018 A | 11/1999 |
| JP | H11514081 A | 11/1999 |
| JP | 3003543 B2 | 1/2000 |
| JP | 2001502542 A | 2/2001 |
| JP | 2001248842 A | 9/2001 |
| JP | 2002527153 A | 8/2002 |
| JP | 2003024036 A | 1/2003 |
| JP | 3093201 U | 4/2003 |
| JP | 2003226577 A | 8/2003 |
| JP | 2004097617 A | 4/2004 |
| JP | 2004512907 A | 4/2004 |
| JP | 2004332069 A | 11/2004 |
| JP | 2005013092 A | 1/2005 |

(56) References Cited

FOREIGN PATENT DOCUMENTS

| | | |
|---|---|---|
| JP | 2005034021 A | 2/2005 |
| JP | 2005514991 A | 5/2005 |
| JP | 2005138773 A | 6/2005 |
| JP | 2005524067 A | 8/2005 |
| JP | 2005533770 A | 11/2005 |
| JP | 2005537918 A | 12/2005 |
| JP | 2005537919 A | 12/2005 |
| JP | 2005538149 A | 12/2005 |
| JP | 2005538159 A | 12/2005 |
| JP | 2006305336 A | 11/2006 |
| JP | 2007057532 A | 3/2007 |
| JP | 2007097787 A | 4/2007 |
| JP | 2007512880 A | 5/2007 |
| JP | 2007297124 A | 11/2007 |
| JP | 2008501406 A | 1/2008 |
| JP | 2008544834 A | 12/2008 |
| JP | 2009509523 A | 3/2009 |
| JP | 2009526714 A | 7/2009 |
| JP | 2009529871 A | 8/2009 |
| JP | 2009537119 A | 10/2009 |
| JP | 2010080261 A | 4/2010 |
| JP | 2011087569 A | 5/2011 |
| JP | 2011515093 A | 5/2011 |
| JP | 2011518567 A | 6/2011 |
| JP | 2012013247 A | 1/2012 |
| JP | 2012026933 A | 2/2012 |
| JP | 2012029633 A | 2/2012 |
| JP | 2012057859 A | 3/2012 |
| JP | 2012506263 A | 3/2012 |
| JP | 2012223190 A | 11/2012 |
| JP | 2012249854 A | 12/2012 |
| JP | 2013516159 A | 5/2013 |
| JP | 2013521075 A | 6/2013 |
| JP | 2013545473 A | 12/2013 |
| JP | 2014501107 A | 1/2014 |
| JP | 2014511175 A | 5/2014 |
| JP | 2014516624 A | 7/2014 |
| JP | 2014520542 A | 8/2014 |
| JP | 2014524313 A | 9/2014 |
| JP | 2014525251 A | 9/2014 |
| JP | 2015500025 A | 1/2015 |
| JP | 2015505476 A | 2/2015 |
| JP | 2015506182 A | 3/2015 |
| JP | 2015513970 A | 5/2015 |
| JP | 2015521847 A | 8/2015 |
| JP | 2016510994 A | 4/2016 |
| JP | 2016520061 A | 7/2016 |
| JP | 2017518033 A | 7/2017 |
| JP | 2017522868 A | 8/2017 |
| JP | 2017525348 A | 9/2017 |
| JP | 6507248 B2 | 4/2019 |
| KR | 1992017172 A | 9/1992 |
| KR | 100244670 B1 | 2/2000 |
| KR | 20050037919 A | 4/2005 |
| KR | 20090008142 U | 8/2009 |
| KR | 20100006995 U | 7/2010 |
| KR | 20110006928 U | 7/2011 |
| KR | 20120025569 A | 3/2012 |
| KR | 20120070731 A | 7/2012 |
| KR | 20120104183 A | 9/2012 |
| KR | 20130004985 A | 1/2013 |
| KR | 20130006714 A | 1/2013 |
| KR | 20130006714 U | 11/2013 |
| KR | 200470732 Y1 | 1/2014 |
| KR | 20140128449 A | 11/2014 |
| KR | 101955000 B1 | 3/2019 |
| KR | 102148901 B1 | 8/2020 |
| NL | 6617184 A | 6/1967 |
| PH | 12017500957 B1 | 10/2017 |
| RU | 2311859 C2 | 12/2007 |
| RU | 2328192 C1 | 7/2008 |
| RU | 2330314 C2 | 7/2008 |
| RU | 2333014 C2 | 9/2008 |
| RU | 2336001 C2 | 10/2008 |
| RU | 2360583 C1 | 7/2009 |
| RU | 89927 U1 | 12/2009 |
| RU | 94815 U1 | 6/2010 |
| RU | 103281 U1 | 4/2011 |
| RU | 115629 U1 | 5/2012 |
| RU | 121706 U1 | 11/2012 |
| RU | 122000 U1 | 11/2012 |
| RU | 124120 U1 | 1/2013 |
| RU | 2476331 C1 | 2/2013 |
| RU | 132318 U1 | 9/2013 |
| RU | 2509516 C2 | 3/2014 |
| UA | B8052 C2 | 9/2009 |
| UA | 89752 C2 | 3/2010 |
| UA | 67598 U | 2/2012 |
| UA | 78167 U | 3/2013 |
| WO | WO9503050 A2 | 2/1995 |
| WO | 9527412 A1 | 10/1995 |
| WO | 9632854 A2 | 10/1996 |
| WO | 9748293 A1 | 12/1997 |
| WO | 9817131 A1 | 4/1998 |
| WO | 0009188 A1 | 2/2000 |
| WO | 0021598 A1 | 4/2000 |
| WO | 0028842 A1 | 5/2000 |
| WO | 0050111 A1 | 8/2000 |
| WO | 0102040 A1 | 1/2001 |
| WO | WO-0122907 A1 | 4/2001 |
| WO | WO 2000122907 A1 | 4/2001 |
| WO | 02051468 A2 | 7/2002 |
| WO | 02058747 A1 | 8/2002 |
| WO | 02060769 A1 | 8/2002 |
| WO | 03005045 A1 | 1/2003 |
| WO | 03028409 A1 | 4/2003 |
| WO | 03050405 A1 | 6/2003 |
| WO | 03059424 A1 | 7/2003 |
| WO | WO-03055486 A1 | 7/2003 |
| WO | 03083283 A1 | 10/2003 |
| WO | WO 2003/101454 | 12/2003 |
| WO | 2004022128 A2 | 3/2004 |
| WO | 2004022242 A1 | 3/2004 |
| WO | 2004022243 A1 | 3/2004 |
| WO | WO 2004029050 A1 | 4/2004 |
| WO | 2004065348 A1 | 8/2004 |
| WO | WO 2004076289 | 9/2004 |
| WO | WO2004076412 A2 | 9/2004 |
| WO | WO-2004076289 A3 | 12/2004 |
| WO | WO2005004989 A2 | 1/2005 |
| WO | WO2005039531 A1 | 5/2005 |
| WO | WO2005075452 A1 | 8/2005 |
| WO | WO2005089728 A2 | 9/2005 |
| WO | 2005106350 A2 | 11/2005 |
| WO | WO2005108389 | 11/2005 |
| WO | 2005120614 A1 | 12/2005 |
| WO | WO 2006/004646 A1 | 1/2006 |
| WO | WO2006008108 A2 | 1/2006 |
| WO | WO2006034833 A1 | 4/2006 |
| WO | WO2006073366 A1 | 7/2006 |
| WO | 2006082571 A1 | 8/2006 |
| WO | WO2007002597 A2 | 1/2007 |
| WO | 2007040941 A1 | 4/2007 |
| WO | 2007042941 A2 | 4/2007 |
| WO | WO2007038215 A1 | 4/2007 |
| WO | 2007108877 A2 | 9/2007 |
| WO | 2007131448 A1 | 11/2007 |
| WO | 2007131449 A1 | 11/2007 |
| WO | 2007141668 A2 | 12/2007 |
| WO | 2008006048 A2 | 1/2008 |
| WO | 2008015918 A1 | 2/2008 |
| WO | 2008038144 A2 | 4/2008 |
| WO | WO2008073942 A2 | 6/2008 |
| WO | 2008104870 A1 | 9/2008 |
| WO | WO-2009001085 A2 | 12/2008 |
| WO | WO2009007767 A1 | 1/2009 |
| WO | WO2009007768 A1 | 1/2009 |
| WO | WO2009007769 A1 | 1/2009 |
| WO | WO2009007770 A1 | 1/2009 |
| WO | WO2009007771 A1 | 1/2009 |
| WO | 2009015410 A1 | 2/2009 |
| WO | WO-2009079641 A2 | 6/2009 |
| WO | 2009092419 A2 | 7/2009 |
| WO | 2009092862 A1 | 7/2009 |

(56) References Cited

FOREIGN PATENT DOCUMENTS

| | | |
|---|---|---|
| WO | 2009092419 A3 | 9/2009 |
| WO | 2009118085 A1 | 10/2009 |
| WO | 2009132793 A1 | 11/2009 |
| WO | 2009135729 A1 | 11/2009 |
| WO | 2010045670 A1 | 4/2010 |
| WO | 2010045671 A1 | 4/2010 |
| WO | WO2011045609 | 10/2010 |
| WO | WO 2011/034723 | 3/2011 |
| WO | 2011050943 A1 | 5/2011 |
| WO | 2011050964 A1 | 5/2011 |
| WO | 2011079932 A1 | 7/2011 |
| WO | WO-2011109849 A1 | 9/2011 |
| WO | 2011137453 A2 | 11/2011 |
| WO | WO2011139684 | 11/2011 |
| WO | WO2011139811 | 11/2011 |
| WO | 2012025496 A1 | 3/2012 |
| WO | 2012065310 A1 | 5/2012 |
| WO | 2012065754 A2 | 5/2012 |
| WO | 2012085203 A1 | 6/2012 |
| WO | 2012085207 A1 | 6/2012 |
| WO | 2012106739 A1 | 8/2012 |
| WO | 2012114082 A1 | 8/2012 |
| WO | WO2012110819 | 8/2012 |
| WO | WO-2012134380 A1 | 10/2012 |
| WO | WO 2012142293 | 10/2012 |
| WO | 2013013808 A1 | 1/2013 |
| WO | 2013025921 A1 | 2/2013 |
| WO | 2013034452 A1 | 3/2013 |
| WO | 2013034453 A1 | 3/2013 |
| WO | 2013034460 A1 | 3/2013 |
| WO | 2013045942 A2 | 4/2013 |
| WO | 2013057185 A1 | 4/2013 |
| WO | 2013082173 A1 | 6/2013 |
| WO | 2013083631 A1 | 6/2013 |
| WO | 2013098395 A1 | 7/2013 |
| WO | 2013116571 A1 | 8/2013 |
| WO | 2013116572 A1 | 8/2013 |
| WO | WO 2013/110210 * 8/2013 ............ A61M 15/06 | |
| WO | WO-2013116558 A1 | 8/2013 |
| WO | WO-2013116561 A1 | 8/2013 |
| WO | 2013142671 A1 | 9/2013 |
| WO | 2013152873 A1 | 10/2013 |
| WO | 2013178769 A1 | 12/2013 |
| WO | 2013189050 A1 | 12/2013 |
| WO | 2013189052 A1 | 12/2013 |
| WO | 2014005275 A1 | 1/2014 |
| WO | 2014012906 A1 | 1/2014 |
| WO | 2014012907 A1 | 1/2014 |
| WO | 2014015463 A1 | 1/2014 |
| WO | WO-2014004648 A1 | 1/2014 |
| WO | 2014061477 A1 | 4/2014 |
| WO | 2014071329 A1 | 5/2014 |
| WO | 2014130695 A1 | 8/2014 |
| WO | 2014140320 A1 | 9/2014 |
| WO | 2014150131 A1 | 9/2014 |
| WO | WO-2014150245 A1 | 9/2014 |
| WO | WO-2014151434 A2 | 9/2014 |
| WO | WO-2014159240 A1 | 10/2014 |
| WO | WO2014159250 A1 | 10/2014 |
| WO | WO 2014/182736 A1 | 11/2014 |
| WO | WO-2014177859 A1 | 11/2014 |
| WO | WO-2014190079 A2 | 11/2014 |
| WO | WO 2015/009862 A2 | 1/2015 |
| WO | WO 2015/054885 * 4/2015 ............. A24F 40/40 | |
| WO | WO2015054885 A1 | 4/2015 |
| WO | WO 2015/084544 | 6/2015 |
| WO | WO-2015091258 A1 | 6/2015 |
| WO | 2015114327 A1 | 8/2015 |
| WO | 2015114328 A1 | 8/2015 |
| WO | 2015149404 A1 | 10/2015 |
| WO | 2015165812 A1 | 11/2015 |
| WO | WO-2015167629 A1 | 11/2015 |
| WO | WO-2015179292 A1 | 11/2015 |
| WO | WO2016071705 | 11/2015 |
| WO | WO2016071706 | 11/2015 |
| WO | 2015189623 A1 | 12/2015 |
| WO | 2015198049 A1 | 12/2015 |

OTHER PUBLICATIONS

Application and File History for U.S. Appl. No. 15/525,194, filed May 8, 2017, Inventor; Mcadam et al.

Great Britain Search Report, Application No. GB 1419865.9, dated May 7, 2015, 4 pages.

Written Opinion of International Preliminary Examining Authority, International Application No. PCT/GB2015/053368, dated Oct. 4, 2016, 7 pages.

International Preliminary Report on Patentability, International Application No. PCT/GB2015/053368, dated Feb. 3, 2017, 8 pages.

International Search Report and Written Opinion, PCT/GB2015/053368, dated Jan. 15, 2016, 12 pages.

Britton M et al, Impact of health technology assessments, some experiences of SBU, Int J Technol Assess Health Care, Fall 2002, vol. 18 No. 4 pp. 824-831.

Chakraborty S, Mediated electrocatalytic oxidation of bioanalytes and biosensing of glutamate using functionalized multiwall carbon nanotubes—biopolymer nanocomposite, Journal of Electroanalytical Chemistry, Nov. 1, 2007, vol. 609, No. 2, pp. 155-162.

Cymes G D, The unanticipated complexity of the selectivity-filter glutamates of nicotinic receptors, Nature Chemical Biology, Dec. 2012, vol. 8, No. 12, pp. 975-981.

Dankwa E et al., Aids to smoking cessation, New Zealand Medical Journal, Apr. 11, 1997, vol. 110, No. 1041 pp. 131-132.

Durazzo T C, Chronic cigarette smoking in alcohol dependence: associations with cortical thickness and N-acetylasparate levels in the extended brain reward system, Addict Biology, Mar. 2013, vol. 18, No. 2, pp. 379-391.

Giannos S A, Temporally controlled drug-delivery systems—coupling of pH oscillators with membrane-diffusion, Journal of Pharmaceutical Sciences, May 1995, vol. 84, No. 5, pp. 539-543.

Glueck C J, Nonpharmacologic and pharmacologic alternation of high-density lipoprotein cholesterol: therapeutic approaches to prevention of atherosclerosis, Am Heart Journal, Nov. 1985, vol. 110, No. 5, pp. 1107-1115.

Kalantari-Dehaghi M et al., Mechanisms of mitochondrial damage in keratinocytes by pemphigus vulgaris antibodies, Journal of Biological Chemistry, Jun. 7, 2013, vol. 288, No. 23, pp. 16916-16925.

Kovacic P et al., Iminium metabolite mechanism of nicotine toxicity and addiction: oxidative stress and electron transfer, Medical Hypotheses, 2005, vol. 64, No. 1, pp. 104-111.

Li D M, Catalytic Mechanism of Cytochrome P450 for 5'-Hydroxylation of nicotine: fundamentl reaction pathways and stereoselectivity, Journal of American Chemical Society, May 18, 2011, vol. 133, No. 19, pp. 7416-7427.

Mashhoon T et al., Anterior cingulate proton spectorscopy glumate levels differ as a function of smoking cessation outcome, Prog Neuropsychoparmacol Biol Psychiatry, Aug. 15, 2011, vol. 35, No. 7, p. 1709-1713.

Newton G D et al., New OTC drugs and devices 2002, a selective review, J Am Pharm Assoc, Mar.-Apr. 2004, vol. 44, No. 2, p. 211-225.

O'Neill J et al., Thalamic glutamate decreases with cigarette smoking, Psychopharmacology, (Berlin), Feb. 18, 2014, Epub ahead of print)—Jul. 2014 231(13) pp. 2717-2724.

Pankow J F, Conversion of nicotine in tobacco smoke to its volatile and available free-base form through the action of gaseous ammonia, Environmental Science & Technology, Aug. 1997, vol. 31 No. 8, pp. 2428-2433.

Pankow J F, Percent free base nicotine in the tobacco smoke particulate matter of selected commercial and reference cigarettes, Chemical Research in Toxicology, Aug. 2003, vol. 16, No. 8, pp. 1014-1018.

Patel S U, Structural studies of Impatiens balsamina antimicrobial protein (Ib-AMP1), Biochemistry, Jan. 27, 1998, vol. 37, No. 4, pp. 983-990.

(56) References Cited

OTHER PUBLICATIONS

Petrov E G et al., Two-electron transfer reactions in proteins: bridge-mediated and proton-assisted processes, Phys Rev E Stat Nonlin Soft Matter Phys, Dec. 2003, vol. 68, part 1, 061916, epub Dec. 31, 2003.
Pinggera G M, Urinary acetonitrile concentrations correlate with recent smoking behaviour, BJU International vol. 95, No. 3, p. 306-309.
Pongjanyakul T and Kanjanabat S (2012) AAPS PharmSciTech 13(2): 674-685. Influence of pH modifiers and HPMC viscosity grates on nicotine-magnesium aluminium silicate complex loaded buccal matrix tablets.
Pongjanyakul T and Suksri H (2009) Colloids and Surfaces B: Biointerfaces 74: 103-113. Alginate-magnesium aluminium silicate films for buccal delivery of nicotine.
Sami P, Studies on electron transfer reactions of Keggin-type mixed addenda heteropolytungstovanadophosphates with NADH, Journal of Chemical Sciences, Mar. 2009, vol. 121, No. 2, pp. 155-161.
Vlachou S et al., Both GABA(B) receptor activation and blockage exacerbated anhedonic aspects of nicotine withdrawal in rats, Eur J Pharmacol., Mar. 25, 2011, vol. 655, No. 1-3, pp. 52-58.
Morie G P, Fractions of protonate and unprotonated nicotine in tobacco smoke at various pH, Tobacco Science, 167 (1972) 56 (ISSN: 0082-4623).
Armitage A K, D K Turner, Absorption of nicotine in cigarette and cigar smoke through the oral mucosa, Nature, 226 (1970) pp. 1231-1233.
Federal Register, Federal Register Doc .99-7022, Mar. 23, 1999, 14,086-14,096.
Clayton P M et al., Spectroscopic investigations into the acid-base properties of nicotine at different temperatures, Anal. Methods, 2013, 5, pp. 81-88.
Clayton P M et al., Use of chiroptical spectroscopy to determine the ionisation status of (S)-niotine in e-cigarette formulations and snus, ST49, Coresta Congress, Quebec City, Canada, Oct. 12-16, 2014. Available at: http://www.bat-science.com/groupms/sites/BAT_9GVJXS.nsf/vwPagesWebLive/DO9PVC3G/$ File/Coresta_PC_2014.pdf.
Great Britain Search Report, Application No. GB1419866.7, dated May 7, 2015, 4 pages.
Chinese Office Action, Application No. 201580060720.X, dated Dec. 4, 2017, 17 pages (35 pages with translation).
Japanese Office Action, Application No. 2017-523310, dated Apr. 10, 2018, 2 pages (5 pages with translation).
Application and File History for U.S. Appl. No. 15/525,163, filed May 8, 2017, Inventors: McAdam et al.
Chilean Office Action, Application No. 201701137, dated Aug. 20, 2018, 11 pages.
Chilean Office Action, Application No. 201701108, dated Aug. 20, 2018, 11 pages.
Russian Office Action, Application No. 2018111280, dated Dec. 10, 2018, 8 pages.
Korean Office Action, Application No. 10-2017-7012228, dated Oct. 22, 2018, 7 pages.
Korean Office Notice of Allowance, Application No. 10-2017-7012228, dated Apr. 28, 2019, 3 pages (4 pages with translation).
English Translation of Japanese Search Report, Application No. 2017-523310, dated Jan. 23, 2018, 8 pages.
Korean Office Action, Application No. 10-2017-7012229, dated Oct. 22, 2018, 10 pages.
Chinese Search Report, Application No. 201580061121.X, dated Jan. 23, 2018.
Epperson, *Sex, GABA, and Nicotine: The Impact of Smoking on Cortical GABA Levels Across the Menstrual Cycle as Measured with Proton Magnetic Resonance Spectroscopy*, Biol Psychiatry. Jan. 1, 2005, 12 pages.
International Preliminary Report on Patentability, International Application No. PCT/GB2015/053369, dated Oct. 7, 2016, 7 pages.
International Search Report and Written Opinion, International Application No. PCT/GB2015/053369, dated Feb. 5, 2016, 12 pages.
Villégier AS, Blanc G, Glowinski J, Tassin JP (Sep. 2003). "Transient behavioral sensitization to nicotine becomes long-lasting with monoamine oxidases inhibitors". Pharmacol. Biochem. Behav. 76 (2): 267-74. doi:10.1016/S0091-3057(03)00223-5. PMID 14592678.
Amsterdam, J. V.; Talhout, R.; Vleeming, W.; Opperhuizen, A. (2006). "Contribution of monoamine oxidase (MAO) inhibition to tobacco and alcohol addiction". Life Sciences 79 (21): 1969-1973. doi:10.1016/j.lfs.2006.06.010. PMID 16884739.
Poindexter, E.H. Jr, Carpenter, R.D. 1962. "The isolation of harmane and norharmane from tobacco and cigarette smoke." Phytochemistry, 1(3): 215-221.
Berlin, I.; m. Anthenelli, R. (2001). "Monoamine oxidases and tobacco smoking". The International Journal of Neuropsychopharmacology 4 (1): 33-42. doi:10.1017/S1461145701002188. PMID 11343627.
Fowler, J. S.; Volkow, N. D.; Wang, G. J.; Pappas, N.; Logan, J.; Shea, C.; Alexoff, D.; MacGregor, R. R.; Schlyer, D. J.; Zezulkova, I.; Wolf, A. P. (1996). "Brain monoamine oxidase a inhibition in cigarette smokers". Proceedings of the National Academy of Sciences of the United States of America 93 (24): 14065-14069, doi:10.1073/pnas.93.24.14065. PMC 19495, PMID 8943061.
Fowler, J. S.; Volkow, N. D.; Wang, G.-J.; Pappas, N.; Logan, J.; MacGregor, R.; Alexoff, D.; Shea, C.; Schlyer, D.; Wolf, A. P.; Warner, D.; Zezulkova, I.; Cilento, R. (1996). "Inhibition of monoamine oxidase B in the brains of smokers". Nature 379 (6567): 733-736. doi:10.1038/379733a0. ISSN 0028-0836. PMID 8602220.
Zhang, L., Ashley, D. L., Watson, C. H., Quantitative Analysis of Six Heterocyclic Aromatic Amines in Mainstream Cigarette Smoke Condensate Using Isotope Dilution Liquid Chromatography—Electrospray Ionization Tandem Mass Spectrometry, Nicotine & Tobacco Research (2010) vol. 13, No. 2, pp. 120-126 doi: 10.1093/ntr/ntq219.
Japanese Decision to Grant, Application No. 2017-523309, dated Jul. 24, 2018, 3 pages (6 pages with translation.).
Mil-G-45204 Military Specification: Gold Plating, Electrodeposited (Jun. 7, 1983) [S/S by MIL-DTL-45204D], 18 pages, dated Jun. 7, 1983.
ASTM, *Standard Specification for Electrodeposited Coatings* of Gold *for Engineering Uses*, B488-11 (2011), 6 pages.
SAE, *AMS 2422F Plating, Gold*, Feb. 6, 2014, 2 pages.
QQ-S-365D Federal Specification: Silver Plating, Electrodeposited, General Requirements For (Jun. 3, 1985), 12 pages.
ASTM, *B700-8 Standard Specification for Electrodeposited Coatings of Silver for Engineering Use*, (2014), 5 pages.
SAE, *AMS 2410K Plating, Silver, Nickel Strike, High Bake*, Apr. 19, 2010, 4 pages.
SAE, *AMS 2411H Plating, Silver, for High Temperature Applications*, Dec. 17, 2013, 4 pages.
SAE, *AMS 2412K Plating, Silver, Copper Strike, Low Bake*, Jan. 26, 2015, 4 pages.
Vapegril, *Silver and Gold E-cigarettes*, vapegrl.com, Available from: http://vapegrl.com/silver-gold-e-cigarettes/, as accessed on Feb. 15, 2016, 8 pages.
Fox, Lindsay, *10 Coolest E-Cig Mods*, ecigarettes reviewed, Jul. 9, 2013 As available from http://ecigarettereviewed.com/coolest-e-cigs-mods and retrieved Nov. 15, 2016, 18 pages.
International Search Report and Written Opinion, Application No. PCT/GB2016/053051, dated Jan. 2, 2017, 13 pages.
Written Opinion, Application No. PCT/GB2016/053051, dated Aug. 16, 2017, 7 pages.
Great Britain Search Report, Application No. GB1517361.0, dated Feb. 8, 2016, 5 pages.
Communication pursuant to Article 94(3) EPC for Application No. 16777777.0, dated Jun. 15, 2020, 9 pages.
International Preliminary Report on Patentability for Appl. No. PCT/GB2016/053051, dated Nov. 27, 2017, 7 pages.
Notification of First Office Action for Chinese Application No. 2018103833246, dated Jun. 3, 2020, 21 pages.
Search Report date Jan. 21, 2020 for Chinese Application No. 201680056890.5, 2 pages.

(56) References Cited

OTHER PUBLICATIONS

Abstract of Keithl Y L. et al., Industry research on the use and effects of levulinic acid: a case study in cigarette additives., Nicotine Tobacco Research, Oct. 2005, vol. 7(5), pp. 761-771.
Anonymous, "eGo-C User Manual Changeable System", Shenzhen Joyetech Co. Ltd, 17 pages.
Anonymous, "the eRoll User Manual", Shenzhen Joyetech Co. Ltd, 9 pages.
Application and File History for U.S. Appl. No. 15/764,612, filed Mar. 29, 2018, Inventors: McAdam et al., 319 pages.
Barr P., "Technical Anaylsis of Joyetech eRoll cartridge and Joyetech eGo-C cartridge," Nov. 12, 2019, 3 pages.
Barsanti K C et al., Tobacco smoke particulate matter chemistry by NMR, Magnetic Resonance in Chemistry, 2007, vol. 45, pp. 167-170.
Bringing attention to e-cigarette pH as in important element for research and regulation, Tobacco Control, vol. 24 No. 4, May 14, 2014, 2 pages.
C. Maier, Polypropylene: The Definitive User's Guide and Databook, Elsevier, (19980000), pp. 122-124, XP055656080.
Certified Priority document of WO2015091258, Priority No. EP13198390.0, Priority date: Nov. 12, 2013, 26 pages.
Chinese Office Action and Search Report, Chinese Application No. 201810383324.6, dated Jun. 3, 2020, 21 pages.
Clayton P.M et al., "Use of Chiroptical Spectroscopy to Determine the Ionisation Status of (S)-Nicotine in electronic Cigarette formulations and snus", ST49, Coresta Congress, Quebec City, Canada, Oct. 12-16, 2014, Abstract, 1 page.
Clayton P.M et al., "Use of Chiroptical Spectroscopy to Determine the Ionisation Status of (S)-Nicotine in Electronic Cigarette formulations and Snus", ST49, Coresta Congress, Quebec City, Canada, Oct. 12-16, 2014, Poster.
"Consolidated list of citations—EP3214957," Nov. 19, 2019, 4 pages.
Corrected Affidavit of Andrew Allan Burton, Oct. 15, 2021, Submitted in Counterpart Application EP 3491941, 8 pages.
CRC Handbook of Chemistry and Physics 1989-1990.
Declaration by Connor Bruton dated Feb. 27, 2020 filed on the corresponding US application, U.S. Appl. No. 15/525,163 (some pages have been incorrectly labelled U.S. Appl. No. 15/525,163).
"Declaration of John McKeon," European Patent Application No. 15794254.1 (EP3214957B), Opposition: Nerudia Limited, Nov. 12, 2019, 1 page.
"Declaration of Joseph P. Hamilton," Hamilton Declaration, Nov. 8, 2019, 7 pages.
Declaration of Marc Doring, Nov. 12, 2019, 10 pages.
"Declaration of Sara Luisa Mellor de Sousa," European Patent Application No. 15794254.1 (EP3214957B), Opposition: Nerudia Limited, Nov. 11, 2019, 1 page.
Duell A K., et al., "Free-base Nicotine Determination in Electronic Cigarette Liquids by 1H NMR Spectroscopy," Chemical Research in Toxicology, 2018, vol. 31, pp. 431-434.
El-Hellani A et al., Quantification of free-base and protonated nicotine in electronic cigarette liquids and aerosol emissions, Chemical Research in Toxicology, Aug. 17, 2015, vol. 28(8) pp. 1532-1537.
European Commission Directorate-General for Health & Consumers, Scientific Committee on Emerging and Newly Identified Health Risks, SCENIHR, Addictiveness and Attractiveness of Tobacco Additives, written procedure, Jul. 6, 2010, 112 pages.
European Patent Office Boards of Appeal Datasheet for the Decision for T405/13, Application No. 03077709.8, Apr. 9, 2014, 15 pages.
Ev Stockel, Technical Report, Nov. 8, 2019, 3 pages.
Ev Stockel, Technical Report on Absorption Behaviour of Protonated Nicotine, Jul. 9, 2020, 5 pages.
Extended European Search Report for Application No. 20183945.3, dated Oct. 13, 2020, 8 pages.
Extended European Search Report for European Application No. 18212381.0, dated Apr. 15, 2019, 6 pages.
Extraction from the Register of European Patents of WO2015091258 downloaded Dec. 11, 2019, 1 pages.
Goldgenie, "A 24 carat gold-plated electronic cigarette E-cigarette reviews and rankings," Feb. 17, 2014, 6 pages.
Henningfield J.E. et al., "Estimation of available nicotine content of six smokeless tobacco products," Tobacco Control, vol. 4, 1995, pp. 57-61.
Joyetech., Shenzhen Jianyiteke Science & Technology Co Ltd, Edited Drawing and translation, original Oct. 19, 2012, translation Apr. 14, 2021, 2 pages.
Joyetech., Shenzhen Jianyiteke Science & Technology Co Ltd, Oct. 19, 2012, 1 page.
Joyetech, "The eRoll—User Manual," published online on Oct. 5, 2012, 9 pages.
Joytech, "eRoll Starter Kit," eRoll series, E-Cigarette, Printout Wayback Machine for the webpage http://www.joyetech.com/product/details.php?gno-123, Oct. 26, 2014, 4 pages.
JWEI Group., "About JWEI," 2019 (downloaded May 5, 2021), 3 pages.
JWEI Group., "Zoominfo," downloaded May 5, 2021, 3 pages.
Leffingwell, "Leaf Chemistry BA Basic Constituents of Tobacco Leaf and Differences among Tobacco Types", Blackwell Science (Pub), Jan. 1, 1999) XP055326787. Retrieved from the Internet: URL: http: www.leffingwell.com/download/Leffingwell-Tobacco production chemistry and technology.pdf.
Letter Accompanying Corrected Affidavit of Andrew Allan Burton, Oct. 18, 2021, Submitted in Counterpart Application EP 3491941, 1 page.
Matt Richtel, The £-Cigarette Industry, Waiting to Exhale (New York Times, dated Oct. 26, 2013), 8 pages.
Notice of Allowance for Korean Application No. 10-2017-701228, dated Apr. 28, 2019, 4 pages.
Notice of Opposition dated May 25, 2021 for European Application No. 15794253.3 (EP3214956), 19 pages.
Notice of Opposition to EP3214957 B1, filed by George W. Schlich, Nov. 13, 2019, 23 pages.
Notice of Opposition to EP3214957, filed by Plate Schweitzer Zounek, Nov. 13, 2019, 42 pages.
Occupational Health Guideline for Nicotine, U.S. Department of Labor, Occupational Safety and Health Administration, Sep. 1978, 6 pages.
Office Action dated Aug. 5, 2020 for European Application No. 15794254.1, 138 pages.
Opposition to EP3214957, filed by JT International, Bandpay & Greuter, Nov. 13, 2019, 20 pages.
Opposition to EP3214957, filed by Nerudia Limited, Newburn Ellis, Nov. 13, 2019, 29 pages.
Perfetti T A, Structural Study of Nicotine Salts, Beitrage zur Tabakforschung International, Jun. 1983, vol. 12, No. 2, pp. 43-54.
Picture of the atomizer of the "Wick of the eRoll E-Cigarette," Nov. 10, 2019, 2 pages.
"Report on determining the cartridge material of the eRoll E-Cigarette," Analysis of an eRoll cartridge, Annex D4c, Nov. 10, 2019, 3 pages.
Response Filed in Opposition to European Patent No. 3214956 dated Oct. 15, 2021, 17 pages.
Richtel M., "The E-Cigarette Industry, Waiting to Exhale," Wayback Machine archive of Article in New York Times: https://www.nytimes.com/2013/10/27/business/thee-cigarette-industry-waiting-to-exhale.html., Archived on Oct. 28, 2013, NY Times article dated Oct. 26, 2013, XP055656051, 12 pages.
Sastri V.R., "Plastics in Medical Devices: Properties, Requirements and Applications," 2010, pp. 100,226,230.
Screenshot of "Joyetech eRoll Manual," Retreived from the Internet: URL: https://www.joyetech.com/download/?mid=1145, Oct. 5, 2012, 1 page.
Screenshot of the image gallery of the "6th Global Forum on Nicotine," Retrieved from the Internet: URL: https://gfn.net.co/archive/2014-photo-galleries/2014-g2/category/3-gfn2014-g2?start=0, 1 page.
Search Report dated Mar. 8, 2021 for Chinese Application No. 2019101103915, 2 pages.

(56) References Cited

OTHER PUBLICATIONS

Seeman et al., The Form of Nicotine in Tobacco. Thermal Transfer of Nicotine and Nicotine Acid Salts to Nicotine in the Gas Phase, in J Agric Food Chem, 1999, vol. 47, pp. 5133-5145.
Signed Affidavit of Andrew Allan Burton, Oct. 7, 2021, Submitted in Counterpart Application EP 3491941, 8 pages.
"The Vapor Pro" archived Feb. 23, 2014 and available at URL: https://web.archive.org/web/20140223102416/http://www.thevaporpro.com/faq.html.
Thermo Fisher Scientific, Measuring pH of Non-Aqueous and Mixed Samples, Application Note 007, 2014, document reference AN-PHNONAQS-E 1014 Rev A, 4 pages.
Tripathi D., "Practical Guide to Polypropylene," Rapra Technology Ltd, 2002, pp. 58,59,98,99.
U.S. Appl. No. 14/286,552 (priority application for WO2014190079A2 as received by the International Bureau), 90 pages.
Vas C A et al., "Acetoin is a precursor to diacetyl in e-cigarette liquids," Food and Chemical Toxicology, 2019, vol. 133, 110727, 16 pages.
Wayback Machine archive of The Vapor Pro website: http://www.thevaporpro.com/faq.html, Archived on Sep. 11, 2013, 19 pages.
Wikipedia entry for Lik Hon, https://en.wikipedia.org/wiki/Hon Lik, downloaded Oct. 18, 2019, 4 pages.
"Witness Statement Noori Brifcani," (May 6, 2021), 23 pages.
Yao Jason., Email from Jason Yao (Mar. 16, 2021), 1 page.
Deals or Duds, "Why Do Some E-liquids Crack Plastic Tanks?" Apr. 26, 2014, Retrieved from the Internet: https://www.dealsorduds.com/guides/e-liquids-crack-plastic-tanks/, 14 pages.
"Declaration of Adam Bown," Feb. 28, 2022, 160 pages.
"Declaration of Andrew Allan Burton," Oct. 15, 2021, 8 pages.
"Declaration of Andrew Allan Burton," Oct. 7, 2021, 8 pages.
"Declaration of Daniel Myers," Mar. 2, 2022, 9 pages.
"Declaration of William Ward III," Feb. 28, 2022, 24 pages.
"eRoll pictures metadata," Nov. 11, 2019, 6 pages.
Ev Stockel, Technical Report, Jun. 24, 2021, 1 pages.
"Health Risk of BPA in Ecig Products," ECF, Jul. 16, 2013, https://www.e-cigarette-forum.com/threads/health-risk-of-bpa-in-ecig-products.443140/, 4 pages.
Joyetech, "eGo-C Atomizer body," 2019, Retrieved from the Internet: https://www.joyetech.com/product/ego-c-atomizer-body/, 2 pages.
Joyetech, "eGo-C Atomizer head," 2019, Retrieved from the Internet: https://www.joyetech.com/product/ego-c-atomizer-head/, 2 pages.
Joyetech, "eGo-C Starter Kits," 2019, Retreived from the Internet: https://www.joyetech.com/product/ego-c-starter-kit/, 3 pages.
Joyetech, "eGo-T A Type Transparent Empty Cartridge (5Pcs), " 2019, Retrieved from the Internet: https://www.joyetech.com/product/ego-t-a-type-transparent-empty-cartridge5pcs/, 2 pages.
Joyetech, "eRoll Battery," 2019, Retreived from the Internet: https://www.joyetech.com/product/eroll-battery/, 2 pages.
Joyetech, "e-roll Empty Cartridge," 2019, Retreived from the Internet: https://www.joyetech.com/product/eroll-empty-cartridge/, 2 pages.
Joyetech, "e-roll Starter Kits," 2019 Retreived from the internet: https://www.joyetech.com/product/eroll-starter-kit/, 4 pages.
Juul Labs Delivery message, Messenger Receipt 2p - Ball, Krystine, Nov. 11, 2019, 2 pages.
LiteCig USA "Orders and Confirmations," 2013, 13 pages.
Observations on the Grounds of Appeal for European Patent No. 3214957 (15794254.1), mailed Apr. 14, 2022, 21 bages.
Office Action for Ukraine Application No. a201810662, mailed Jul. 22, 2022, 11 pages.
Oral Proceedings for the Opposition of European Patent No. 3214957 (15794254.1), mailed Jun. 25, 2021, 19 pages.
Picture of the atomizer of the "eRoll", Nov. 11, 2019, 6 pages.
Picture of the atomizer of the "eRoll" e-cigarette, Oct. 30, 2019, 2 pages.
Planet of the Vapes, "Look What My Banana Juice Did to my Tank!" Sep. 22, 2012, https://www.planetofthevapes.co.uk/forums/ecig-discussion/general-chat/threads/look-what-my-banana-juice-did-to-my-tank.3083/, 6 pages.

Reply of the patent proprietor to the notice(s) of opposition Patent No. 3491941(18212381), dated Oct. 7, 2021, 30 pages.
Reply to Grounds of Appeal, for European Patent No. 3214957 (15794254.1), mailed Apr. 20, 2022, 45 pages.
Results, Apr. 11, 2019, 2 pages.
Results, May 11, 2019, 1 page.
Spinefuel, "Smoktech 510 Screw Tank & 510 Pro DCTank Combo Review," Sep. 28, 2012, https://spinfuel.com/smoktech-510-screw-tank-510-pro-dctank-combo-review/, 4 pages.
U.S. Appl. No. 61/912,507, filed Dec. 5, 2013, Inventor: Bowen, adam et al., 16 pages.
VaporDNA, "Buy Online Electronic Cigrettes and Accesseories at the Best Possible Prices," https://vapordna.wordpress.com/, Sep. 9, 2014, 12 pages.
Ward, William Juul, Pictures of the "eRoll Battery", email Nov. 11, 2019, 7 pages.
"Chinese First Office Action for Chinese Application No. 200980152395.4 date issued Dec. 3, 2012".
"Chinese Notification of First Office Action for Chinese Application No. 201480031926.5 dated Apr. 21, 2017".
"Chinese Office Action for Chinese Application No. 201480031296.1 dated Mar. 27, 2017".
"Decision to Grant dated Feb. 5, 2018 for Ukraine Application No. a201607243".
"Decision to Grant dated Jun. 23, 2016 for Ukrainian Application No. a201500198".
"Decision to Grant dated Apr. 6, 2016 for Russian Application No. 2015100321".
"Decision to Grant for Russian Application No. 2017105898, dated Mar. 16, 2018".
"Decision to Grant in Russian Application No. 2014120213, dated Oct. 26, 2016".
"Decision to Grant received for Japanese Patent Application No. 2011-532464, mailed on Aug. 5, 2014".
"Decision to Grant received for Japanese Patent Application No. 2016-134648, mailed May 22, 2018".
"Decision to Grant received for Russian Patent Application No. 2011120430, mailed on Apr. 1, 2014".
"European Search Report received for European Patent Application No. 16166656.5 dated Oct. 11, 2016".
"Examination Report mailed Nov. 20, 2019, for Australian Application No. 2017256084".
"Examination Report mailed Jun. 2, 2017, for Australian Application No. 201512626".
"Extended European Search Report for Application No. 19196432.9, mailed on Dec. 9, 2019".
"Extended European Search Report for Application No. 22155057.7, mailed on Jun. 15, 2022".
"Extended European Search Report for Application No. EP17197150.0, mailed on Mar. 1, 2018".
"Extended European Search Report for Application No. 16151458.3, mailed Jul. 11, 2016".
"Extended European Search Report for European Application No. 15178588.8, mailed on Apr. 22, 2016".
"Extended European Search Report received for European Patent Application No. 18205608.5, mailed on Jul. 12, 2019".
"Extended European Search Report received for European Patent Application No. 17189951.1, mailed on Jan. 4, 2018".
"Feature Analysis of Claim 1", BATMark Limited, Opposition Against EP3117860B1, Exhibit D6 , Oct. 30, 2019 , 1 Page (Official Copy Only).
"GB Intention to Grant, Application No. GB1405720.2, dated Sep. 26, 2017".
"Great Britain Examination Report, Application No. GB1405720.2, dated Jun. 27, 2017".
"Hong Kong Publication, Application No. 14110165.2, published Dec. 19, 2014".
"Hong Kong Publication, Application No. 16113324.2, published Oct. 6, 2017".
"Integrating Electrical Heating Elements in Product Design", Metallic Resistance Heating Wire, Chapter 1, Section 1.4, resulting in interlocutory decision dated Aug. 7, 2019 , 1 page.

(56) References Cited

OTHER PUBLICATIONS

"Integrating Electrical Heating Elements in Product Design", Metallic Resistance Heating Wire, resulting in interlocutory decision dated Aug. 7, 2019, 8 pages.
"International Preliminary Report on Patentability for Application No. PCT/AT2009/000413, mailed on May 5, 2011".
"International Preliminary Report on Patentability for Application No. PCT/AT2009/000414, mailed on Apr. 26, 2011".
"International Preliminary Report on Patentability for Application No. PCT/AT2012/000017, issued on Aug. 13, 2013".
"International Preliminary Report on Patentability for Application No. PCT/EP2012/003103, mailed on Feb. 6, 2014".
"International Preliminary Report on Patentability for Application No. PCT/EP2012/070647, mailed on May 1, 2014".
"International Preliminary Report on Patentability for Application No. PCT/GB2014/051332, mailed on Nov. 12, 2015".
"International Preliminary Report on Patentability for Application No. PCT/GB2014/051333, completed on Aug. 5, 2015".
"International Preliminary Report on Patentability for Application No. PCT/GB2014/051334, mailed on Nov. 12, 2015".
"International Preliminary Report on Patentability for Application No. PCT/GB2015/050195 mailed May 13, 2016".
"International Preliminary Report on Patentability for Application No. PCT/GB2015/053445, mailed on Jan. 24, 2017".
"International Preliminary Report on Patentability for Application No. PCT/GB2017/051139, completed on Aug. 6, 2018".
"International Preliminary Report on Patentability for corresponding International Application No. PCT/GB2015/051213 mailed on Jul. 14, 2016".
"International Preliminary Report on Patentability for International Application No. PCT/GB2014/051688 mailed on Dec. 17, 2015".
"International Preliminary Report on Patentability mailed Sep. 9, 2014 for Application No. PCT/EP2013/064922, filed Jul. 15, 2013".
"International Preliminary Report on Patentability received for International Application No. PCT/GB2014/051633 mailed Oct. 23, 2015".
"International Search Report and Written Opinion for Application No. PCT/GB2015/053445, mailed on Apr. 18, 2016".
"International Search Report and Written Opinion for Application No. PCT/GB2017/051139, mailed on Aug. 9, 2017".
"International Search Report and Written Opinion mailed Oct. 11, 2013 for Application No. PCT/EP2013/064922, filed Jul. 15, 2013".
"International Search Report and Written Opinion received for PCT Application No. PCT/EP2012/003103, mailed on Nov. 26, 2012".
"International Search Report and Written Opinion received for PCT Application No. PCT/GB2014/051333, mailed on Jul. 17, 2014".
"International Search Report and Written Opinion received for PCT Application No. PCT/GB2014/051334 mailed Jul. 21, 2014".
"International Search Report and Written Opinion received for PCT Patent Application No. PCT/GB2014/051332, mailed on Jul. 21, 2014".
"International Search Report and Written Opinion received for PCT Patent Application No. PCT/EP2012/070647, mailed on Feb. 6, 2013".
"International Search Report and Written Opinion received for PCT Patent Application No. PCT/AT2012/000017, mailed on Jul. 3, 2012".
"International Search Report for Application No. PCT/GB2015/050195, mailed Sep. 2, 2015".
"International Search Report for corresponding International Application No. PCT/GB2015/051213 mailed on Jul. 16, 2015".
"International Search Report for International Application No. PCT/GB2014/051688 dated Aug. 26, 2014".
"International Search Report of the International Searching Authority for International Application No. PCT/GB2014/051633 mailed Dec. 4, 2014".
"International Search Report received for PCT Patent Application No. PCT/AT2009/000413 mailed on Jan. 25, 2010".
"International Search Report received for PCT Patent Application No. PCT/AT2009/000414 mailed on Jan. 26, 2010".
"Korean Office Action, Korean Application No. 10-2015-7034538, dated May 12, 2017".
"Letter from Patentee for European Application No. 17189951.1, dated Aug. 21, 2018".
"Metallic Resistance Heating Wire", Chapter 1, Integrating Electrical Heating Elements in Product Design, Section 1.1 to 1.3.2, resulting in interlocutory decision dated Aug. 7, 2019, 6 pages.
"Notice of Allowance mailed Dec. 12, 2018 for Korean Application No. 10-2017-7015164".
"Notice of Allowance mailed Oct. 18, 2019 for Korean Application No. 1020167018457".
"Notice of Allowance mailed May 30, 2017 for Korean Application No. 1020157001277".
"Notice of Allowance mailed Jun. 27, 2018 for Korean Application No. 1020167020977".
"Notice of Opposition—Imperial Tobacco Limited for European Application No. 20171293.2, mailed on Nov. 16, 2022".
"Notice of Opposition—Philip Morris for European Application No. 20171293.2, mailed on Nov. 17, 2022".
"Notice of Opposition Letter from EPO Opposition against for EP2358418 mailed on Mar. 1, 2017".
"Notice of Opposition mailed Oct. 30, 2019 for European Application No. 16166656.5".
"Notice of Reasons for Rejection for Japanese Application No. 2020-121265, mailed on Jul. 20, 2021".
"Notice of Reasons for Rejection for Japanese Application No. 2020-121265, mailed on Jun. 21, 2022".
"Notice of Reasons for Rejection received for Japanese Application No. 2020-181572 mailed on Feb. 14, 2023".
"Notice of Reasons for Rejection received for Japanese Patent Application No. 2020-121265, mailed on Apr. 11, 2023".
"Notice of Reasons for Revocation mailed Apr. 17, 2017 for Japanese Patent No. 5960358".
"Notification to Grant Patent Right received for Chinese Patent Application No. 201610086101.4, mailed on Oct. 25, 2018".
"Notification to Grant received for Chinese Patent Application No. 201610256674.7, mailed on Jan. 12, 2023".
"Office Action dated Jul. 2, 2020 for Chinese Application No. 201780020023.0 filed Sep. 25, 2018".
"Office Action dated Nov. 22, 2016 for Canadian Application No. 2878951".
"Office Action dated Nov. 23, 2018 for Korean Application No. 1020167018457".
"Office Action dated Apr. 25, 2017 for Japanese Application No. 2016123816".
"Office Action dated Sep. 3, 2014, for Russian Application No. 2013504605".
"Office Action for Chilean Application No. 201701486 mailed Nov. 11, 2019".
"Office Action For Chinese Application No. 201780020023.0, mailed on Mar. 8, 2021".
"Office Action for European Application No. 16166656.5, mailed on Jul. 29, 2020".
"Office Action For Korean Application No. 10-2018-7031081, mailed on Dec. 15, 2021".
"Office Action mailed Jun. 2, 2016 for Chinese Application No. 201380038075.2".
"Office Action mailed Jun. 15, 2018 for Korean Application No. 10-2017-7015164".
"Office Action mailed Mar. 16, 2020 for Chinese Patent Application No. 201610255788.X, filed Oct. 21, 2009".
"Office Action mailed Jun. 26, 2018 for Japanese Application No. 2017-530762".
"Office Action mailed Nov. 26, 2019 for Brazilian Application No. 112015000872-0".
"Office Action mailed Sep. 27, 2019 for Korean Application No. 10-2019-7005785".
"Office Action mailed Apr. 10, 2019, for Korean Application No. 1020167018457".
"Office Action mailed Apr. 23, 2018 for Chinese Application No. 201580006377.0".
"Office Action mailed Dec. 8, 2017, for Korean Application No. 1020167020977".

(56) References Cited

OTHER PUBLICATIONS

"Office Action mailed Jan. 23, 2018, for Japanese Application No. 2016548373".
"Office Action mailed Jun. 5, 2018, for Chinese Application No. 201610552323.0".
"Office Action mailed Mar. 14, 2018, for Russian Application No. 2016131333".
"Office Action received for Canadian Patent Application No. 2,964,829, mailed on Jun. 5, 2023".
"Office Action received for Chinese Patent Application No. 201480024988.3, mailed on Dec. 30, 2016".
"Office Action received for Chinese Patent Application No. 201480024978.X mailed on Jan. 18, 2017".
"Office Action received for Chinese Patent Application No. 201480024988.3, mailed on Sep. 11, 2017".
"Office Action received for Chinese Patent Application No. 201580022356.8, mailed on Jul. 18, 2018".
"Office Action received for Chinese Patent Application No. 201610086101.4, mailed on May 4, 2018".
"Office Action received for Chinese Patent Application No. 201610371843.1, mailed on Sep. 30, 2018".
"Office Action received for Chinese Patent Application No. 2020105247754, mailed on Feb. 28, 2023".
"Office Action received for European Patent Application No. 17189951.1, mailed on Jan. 25, 2019".
"Office Action received for Japanese Patent Application No. 2016-564977, mailed on Dec. 5, 2017".
"Office Action received for Japanese Patent Application No. 2018-088088 mailed on Feb. 28, 2019".
"Office Action received for Russian Patent Application No. 2014120213, mailed on Sep. 22, 2017".
"Office Action received for Russian Patent Application No. 2015146847, mailed on Sep. 22, 2017".
"Opposition Statement dated Mar. 30, 2017 for Japanese Patent No. 5960358".
"Partial EPO Opposition File Wrapper for EP2871983, resulting in interlocutory decision dated Aug. 7, 2019".
"Reasons for Rejection received for Japanese Patent Application No. 2015-137361, mailed on May 31, 2016".
"Reasons for Rejection received for Japanese Patent Application No. 2011-532464, mailed on Oct. 7, 2013".
"Reasons for Rejection received for Japanese Patent Application No. 2014-179732, mailed on Sep. 8, 2015".
"Reasons for Rejection received for Japanese Patent Application No. 2016-134648 mailed May 23, 2017".
"Russian Decision to Grant, Application No. 2015146845, dated Apr. 27, 2017".
"Russian Office Action, Application No. 2016142584, dated Nov. 21, 2017".
"Search Report for Chilean Application No. 2019-11665, mailed Nov. 11, 2019".
"Search Report for Japanese Application No. 2018-546893, mailed Nov. 21, 2019".
"Search Report mailed Jun. 24, 2019 for Russian Application No. 2018137583".
"Search Report mailed Mar. 28, 2017 for Japanese Patent Application No. 2016-134648".
"Search Report mailed May 29, 2015 for Great Britain Application No. 1422018.0".
"Search Report mailed Mar. 23, 2015, for Great Britain Application No. GB1401520.0".
"Search Report received for Chinese Patent Application No. 201610086101.4, mailed on Apr. 25, 2018".
"Search Report received for Japanese Patent Application No. 2011-532464, mailed on Sep. 19, 2013".
"Search Report received for Japanese Patent Application No. 2014-179732, mailed on Aug. 25, 2015".
"Search Report received for Japanese Patent Application No. 2016-564977, mailed on Oct. 25, 2017".
"Search Report received for Russian Patent Application No. 2015146843/12 (072088), mailed on Apr. 24, 2017".
"Search Report received for Russian Patent Application No. 2018137501, mailed on Apr. 29, 2019".
"Translation of Chinese Second Office Action for Chinese Application No. 200980152395.4 date issued Aug. 20, 2013".
"Translation of Search Report for JP2016517671 date of search Feb. 1, 2017".
"Welcome to Filtrona Porous Technologies", Filtrona Richmond Inc., Available Online at <http://www.filtronaporoustechnologies.com>, Nov. 19, 2018, 1 page.
"Written Opinion for Application No. PCT/AT2009/000413, mailed on Jan. 25, 2010".
"Written Opinion for Application No. PCT/AT2009/000414, mailed on Jan. 26, 2010".
"Written Opinion for International Application No. PCT/GB2014/051688 dated Aug. 26, 2014".
"Written Opinion for PCT Patent Application No. PCT/GB2015/051213 mailed on Jul. 16, 2015".
"Written Opinion of the International Preliminary Examining Authority for Application No. PCT/GB2015/050195 mailed Jan. 20, 2016".
"Written Opinion of the International Preliminary Examining Authority for International Application No. PCT/GB2015/051213 mailed on Mar. 29, 2016".
"Written Opinion of the International Preliminary Examining Authority mailed Jun. 23, 2014 for Application No. PCT/EP2013/064922, filed Jul. 15, 2013".
"Written Opinion of the International Searching Authority for Application No. PCT/GB2015/050195, mailed Sep. 2, 2015".
"Written Opinion of the International Searching Authority for International Application No. PCT/GB2014/051633 mailed Dec. 4, 2014".
Aerosols, "Pulmonary Pharmacology: Delivery Devices and Medications", available at http://www.ceu.org/cecourses/z98107/ch4.htm, Sep. 6, 2017, 2 pages.
Buchberger, "Application and File History for U.S. Appl. No. 15/997,113, filed Jun. 4, 2018".
Buchberger, "Application and File History for U.S. Appl. No. 13/125,343, filed Apr. 21, 2011".
Buchberger, "Application and File History for U.S. Appl. No. 13/984,512, filed Aug. 29, 2013".
Buchberger, "Application and File History for U.S. Appl. No. 14/268,909, filed May 2, 2014".
Buchberger, "Application and File History for U.S. Appl. No. 14/296,803, filed Jun. 5, 2014".
Buchberger, "Application and File History for U.S. Appl. No. 14/306,831, filed Jun. 17, 2014".
Buchberger, "Application and File History for U.S. Appl. No. 15/307,095, filed Oct. 27, 2016".
Buchberger, "Application and File History for U.S. Appl. No. 15/454,156 filed Mar. 9, 2017".
Buchberger, "Application and File History for U.S. Appl. No. 15/470,078, filed Mar. 27, 2017".
Buchberger, "Application and File History for U.S. Appl. No. 15/470,089, filed Mar. 27, 2017".
Buchberger, "Application and File History for U.S. Appl. No. 14/235,210, filed Mar. 4, 2014".
Buchberger, "Application and File History for U.S. Appl. No. 14/353,256, filed Apr. 21, 2014".
Buchberger, "Application and File History for U.S. Appl. No. 14/594,065, filed Jan. 9, 2015".
Buchberger, "Application and File History for U.S. Appl. No. 15/470,095, filed Mar. 27, 2017".
Diener Electronic, "Plasma Technology", The Company Diener Electronic GmbH+Co. KG, www.plasma.de, Oct. 17, 2017, 19 Pages.
Dunn, et al., "Heat Pipes", 4th edition, ISBN 0080419038, 1994, 14 Pages.
ECF, "Welcome to the World's Largest E-Cigarette Website: The Voice of Vaping since 2007", Oct. 2011, Nichrome or Kanthal Specs for Purchasing, retrieved on Apr. 19, 2020.
Fraser, "Application and File History for U.S. Appl. No. 16/096,554, filed Oct. 25, 2018".

(56) References Cited

OTHER PUBLICATIONS

Hegbom, Thor, "Integrating Electrical Heating Elements in Appliance Design", cited in EPO Opposition File Wrapper for EP2871983, resulting in interlocutory decision dated Aug. 7, 2019, 4 pages.

Iatty, "An Idea of the Iatty, Welcome to the World's Largest E-Cigarette Website: The Voice of Vaping since 2007", retrieved on Dec. 17, 2019, p. 24, Post 467, Jun. 2011, 6 p.

Iatty, "An Idea of the Iatty, Welcome to the World's Largest E-Cigarette Website: The Voice of Vaping since 2007", retrieved on Dec. 17, 2019, p. 37, Post 727, Jun. 2011, 6 p.

Iatty, "An Idea of the Iatty, Welcome to the World's Largest E-Cigarette Website: The Voice of Vaping since 2007", retrieved on Dec. 17, 2019, p. 1, Post 1, Apr. 2011, 7 pages.

Iatty, "An Idea of the Iatty, Welcome to the World's Largest E-Cigarette Website: The Voice of Vaping since 2007", retrieved on Dec. 17, 2019, p. 23, Post 443 and 445, Jun. 2011, 7 pages.

Iatty, "E-Cigarette Forum", commentary by Imeothansis and lorderos33, p. 10, May 2009, 2011, 8 pages.

Kynol, "Standard Specifications of Kynol Activated Carbon Fiber Products", published by Kynol, Sep. 19, 2013, 2 pages.

Lord, "Application and File History for U.S. Appl. No. 14/787,946, filed Oct. 29, 2015".

Reevell, "Application and File History for U.S. Appl. No. 14/888,514, filed Nov. 2, 2015".

Reevell, "Application and File History for U.S. Appl. No. 14/888,517, filed Nov. 2, 2015".

Rudolph, G, "The Influence of $CO_2$ on the Sensory Characteristics of the Favor-System", BAT Cigarettenfabriken GmbH, http://legacy.library.ucsf.edu/tid/sla51f00, 24 pages.

Sharafat, et al., "Ceramic Foams: Inspiring New Solid Breeder Materials", 12th International Workshop on Ceramic Breeder Blanket Interactions, Germany, Sep. 16-17, 2004, 22 pages.

Supulveda, et al., "Processing of Cellular Ceramics by Foaming and In Situ Polymerisation of Organic Monomers", Loughborough University Institutional Repository, 1999, 22 pages.

Wikipedia, "Electronic Cigarette", Available at <https://en.wikipedia.org/w/index.php?title=Electronic_cigratte&oldid=284227163>, Apr. 16, 2009, 7 Pages.

wires.co.uk, "Bare Nickel Chrome/Nichrome Section",, 16 pages.

wires.co.uk, "Specialist in Craft Wire",, 5 pages.

* cited by examiner

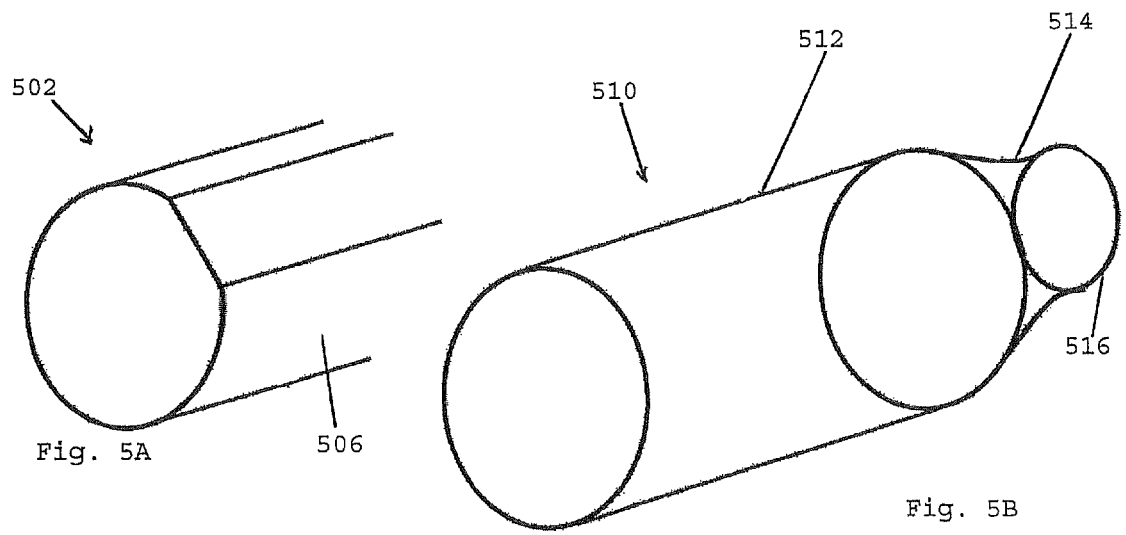
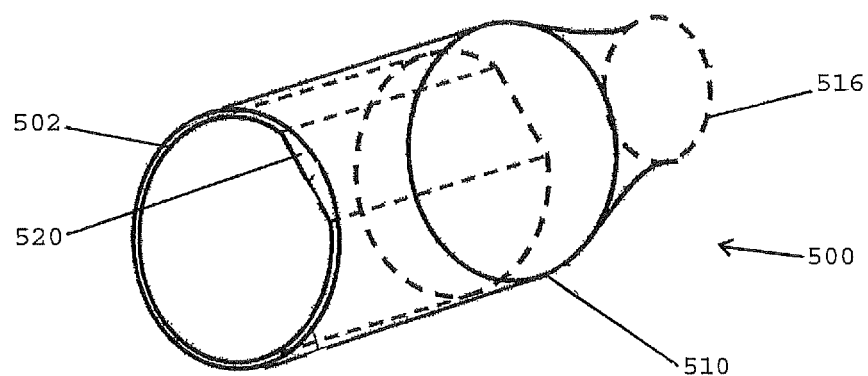
Fig. 5A
Fig. 5B
Fig. 5C
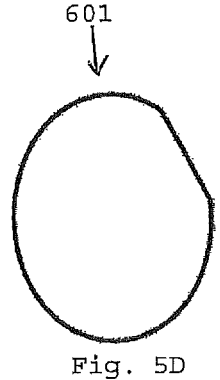
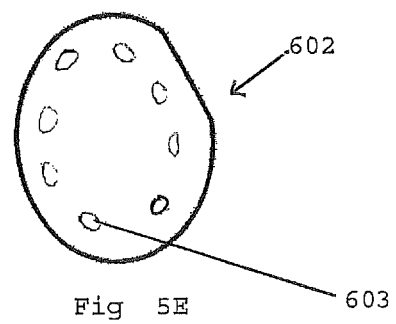
Fig. 5D
Fig 5E

AEROSOL PROVISION SYSTEM

PRIORITY CLAIM

The present application is a National Phase entry of PCT Application No. PCT/GB2016/052831, filed Sep. 14, 2016, which claims priority from GB Patent Application No. 1517092.1, filed Sep. 28, 2015, each of which is hereby fully incorporated herein by reference.

FIELD

The present disclosure relates to aerosol provision cartridges and systems such as nicotine provision systems (e.g. e-cigarettes) comprising coated metallic components. The present disclosure also relates to the use of coated metallic components to stabilize and/or improve the aerosol.

BACKGROUND

Aerosol provision systems such as e-cigarettes generally contain, amongst other parts, an aerosol provision cartridge which comprises a reservoir of a source liquid, typically including nicotine, from which an aerosol is generated, e.g. through vaporization or other means. The aerosol provision cartridge may also comprise an aerosol generating component, such as a heater, which is fluidly connected to the source liquid contained in the reservoir. When a user inhales on the device, the aerosol generating component is activated to vaporize an amount of the source liquid. More particularly, such devices are usually provided with one or more air inlet holes located away from a mouthpiece of the system. When a user sucks on the mouthpiece, air is drawn in through the inlet holes and past the aerosol generating component. There is a flow path connecting between the aerosol generating component and an opening in the mouthpiece so that air drawn past the aerosol generating component continues along the flow path to the mouthpiece opening, carrying some of the aerosol produced from the aerosol generating component with it. The aerosol-carrying air exits the aerosol provision system through the mouthpiece opening for inhalation by the user.

Typical aerosol generating components comprise a heater. The source liquid is generally arranged within the system such that it can access the aerosol generating component. For example, it may be that the aerosol generating component is a wire which is heated during use of the device. As a result of the contact between the source liquid and the wire, when the wire is hearted during use the source liquid is vaporized and subsequently condenses into an aerosol which is then inhaled by the user. The means by which the source liquid can contact the wire may vary. It is not uncommon for the source liquid to be stored in a wadding or other type of holding matrix. This wadding or matrix can either itself directly contact the heating wire or, alternatively, it may be that a further "wick" is in contact with both the wadding and the heating wire. This wick serves to draw the source liquid from the wadding to the heating wire during use.

Other types of systems do not employ wadding to hold the source liquid. Instead, in these systems the source liquid is held freely in a tank or other storage region and is directly fed to the heating wire (which may itself include a wicking core to assist in holding the source liquid in proximity to the wire).

Typically, the aerosol generating component is contained within an aerosol generating region. In some instances, this aerosol generating region is a chamber. The primary characteristics of such a region are that it should provide sufficient space to house the aerosol generating component, as well as to allow for the desired degree of airflow past the aerosol generating component and on to the mouthpiece outlet. Whilst it is desired that substantially all of the vapor that is generated in the aerosol generating region is entrained in the airflow travelling past the aerosol generating component, this does not always occur. For example, in some instances vapor produced in the aerosol generating region can condense and remain within that region. In other words, not all of the vapor produced is entrained in the through-flowing airflow. The result of this is that condensate can accumulate within the aerosol generating region. As a result of the aerosol generating region being provided with an inlet to allow for the ingress of air so as to allow for formation of the aerosol, the aerosol generating region is typically not liquid impermeable—in other words, the aerosol generating region is generally not sealed and as a result any condensate which has accumulated in the aerosol generating region may migrate to other parts of the aerosol provision cartridge. Depending on the composition of the liquid source, this may or may not present certain issues. For example, if the condensate produced from the aerosol generating component contains compounds that are reactive with other components of the aerosol provision cartridge outside of the aerosol generating region, it may be that the acceptability of the aerosol delivered to the user deteriorates over time as a result of the reaction products from the condensate reacting with the other components within the cartridge becoming entrained in the airflow through the device and thus into the resulting aerosol.

Therefore, it would be desirable to provide an aerosol provision cartridge which is able to provide a consistently acceptable aerosol to a user.

SUMMARY

In a first aspect there is provided an aerosol provision cartridge for use with an aerosol provision system, said cartridge comprising: a liquid storage region in fluid communication with an aerosol generating region; and one or more metallic components, located substantially outside of the aerosol generating region and liquid storage region, wherein at least one of the said metallic components has a coating comprising silver and/or gold.

In a further aspect there is provided an aerosol provision cartridge for use with an aerosol provision system, said cartridge comprising: a liquid storage region comprising a source liquid, said source liquid comprising nicotine and at least one acid; an aerosol generating region in fluid communication with the liquid storage region; and one or more metallic components, located substantially outside of the aerosol generating region and liquid storage region, wherein at least one of the said metallic components has a coating comprising silver and/or gold.

In a further aspect there is provided an aerosol provision cartridge for use with an aerosol provision system, said cartridge comprising: a liquid storage region in fluid communication with an aerosol generating region; said aerosol generating region configured to be substantially liquid-free; and one or more metallic components, located substantially outside of the aerosol generating region and liquid storage region, wherein at least one of the said metallic components has a coating comprising silver and/or gold.

It has surprisingly been found that aerosols produced from cartridges and systems of the present disclosure are more acceptable to consumers.

In a further aspect there is provided the use of a metallic component having a coating comprising gold and/or silver in an aerosol provision cartridge to stabilize and/or improve the acceptability of the aerosol to a user.

In a further aspect there is provided a method of preventing the deterioration of the sensorial attributes of an aerosol produced from an aerosol provision cartridge comprising utilizing in the construction of the cartridge a metallic component having a coating comprising gold and/or silver.

In a further aspect there is provided an aerosol provision system comprising an aerosol provision cartridge as defined herein, and an aerosol provision device comprising a power source and an input means.

The approach described herein is not restricted to specific embodiments such as set out below, but includes and contemplates any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Various embodiments will now be described in detail by way of example only with reference to the following drawings:

FIG. 1 is a schematic (exploded) diagram of an aerosol provision system such as an e-cigarette in accordance with some embodiments.

FIG. 2 is a schematic diagram of a main body portion of the e-cigarette of FIG. 1 in accordance with some embodiments.

FIG. 3 is a schematic diagram of an aerosol source portion of the e-cigarette of FIG. 1 in accordance with some embodiments.

FIG. 4 is a schematic diagram showing certain aspects of one end of the main body portion of the e-cigarette of FIG. 1 in accordance with some embodiments.

FIGS. 5A to 5E are schematic diagrams of components of an aerosol provision system in accordance with some other embodiments.

FIG. 6 is an exploded, schematic diagram showing various components of an aerosol provision system in accordance with some other embodiments.

FIG. 7 provides a graph showing user preference levels for aerosols produced from different aerosol provision cartridges.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision cartridge which may form part of an aerosol provision system, such as an e-cigarette. Throughout the following description the term "e-cigarette" is sometimes used; however, this term may be used interchangeably with aerosol (vapor) provision system, or vapor provision device. Further, term "aerosol provision cartridge" may also be referred to as cartomizer, clearomizer or tank, as such terms are common in the field of aerosol provision systems such as e-cigarettes.

FIG. 1 is a schematic diagram of an aerosol/vapor provision system such as an e-cigarette 10 in accordance with some embodiments (not to scale). The e-cigarette 10 has a generally cylindrical shape, extending along a longitudinal axis indicated by dashed line LA, and comprises two main components, namely a body 20 and a cartomizer 30. The cartomizer 30 includes an internal chamber containing a liquid storage region comprising a source liquid from which an aerosol is to be generated, and an aerosol generating component. The cartomizer 30 further includes a mouthpiece 35 having an opening through which a user may inhale the aerosol produced by the aerosol generating component. In this regard, reference to an "aerosol generating component" refers to a component which generates an aerosol either directly or indirectly. For example, where the aerosol generating component is a heater, source liquid may be evaporated and subsequently condense to form an aerosol.

The liquid storage region for the source liquid may comprise a foam matrix or any other structure, such as a wadding, within a housing for retaining the source liquid until such time that it is required to be delivered to the aerosol generating component. Alternatively, the liquid storage region may simply be a reservoir which an amount of "free liquid" contained therein. The liquid storage region may be "closed" or "open". In other words, where the liquid storage region is "closed", the user is not able to re-fill the liquid storage region with liquid once it has been depleted without dismantling or otherwise breaking the device in a manner which is not envisaged by the manufacturer. Where the liquid storage region is "open" it is configured to be re-filled by the user. This "open" configuration can generally be achieved by using a mouthpiece or other component that seals the liquid storage region, but which can be removed (via a screw thread, etc.) such that access to the liquid storage region is provided.

The aerosol generating component includes a heater for vaporizing the source liquid to form the aerosol. The aerosol generating component may further include a wick or similar facility to transport a small amount of the source liquid from the storage region to a heating location on or adjacent the heater.

The body 20 includes a re-chargeable cell or battery to provide power for the e-cigarette 10 and a circuit board for generally controlling the e-cigarette 10. In use, when the heater receives power from the battery, as controlled by the circuit board, the heater vaporizes the source liquid at the heating location to generate the aerosol, and this is then inhaled by a user through the opening in the mouthpiece 35. The aerosol is carried to the mouthpiece 35 along an air channel that connects the aerosol generating region to the mouthpiece 35 opening as a user inhales on the mouthpiece 35.

In this particular example, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer 30 also serves as a socket for connecting a charging device (not shown) when the body 20 is detached from the cartomizer 30. The other end of the charging device can be plugged into an external power supply, for example a USB socket, to charge or to re-charge the cell/battery in the body of the e-cigarette 10. In other implementations, a cable may be provided for direct connection between the electrical connector on the body 20 and the external power supply.

In connection with this, in order to allow for connection with the body 20 (both mechanically and electrically) the cartomizer 30 generally contains one or more metallic components. For example, these components may be screw thread rings, electrodes, or intermediate supporting members (all not shown). When assembled, such metallic components allow for the cartomizer 30 to be connected to the body 20 in a manner which supports the aerosol generating component in the aerosol generating region, allows for the provision of electrical current to the aerosol generating component, and allows for airflow to travel into the aerosol generating region so that it may collect the vapor/aerosol produced therein and deliver it to the user.

The e-cigarette 10 is provided with one or more holes (not shown in FIG. 1) for air inlet. These holes connect to an air running passage through above mentioned metallic components of the e-cigarette 10 to the mouthpiece 35. The air passage includes a region around the aerosol generating region and a section comprising an air channel connecting from the aerosol generating region to the opening in the mouthpiece 35.

When a user inhales through the mouthpiece 35, air is drawn into this air passage through the one or more air inlet holes, which are suitably located on the outside of the e-cigarette 10. This airflow (or the resulting change in pressure) is detected by a pressure sensor (as an example of an input means) that in turn activates the aerosol generating component (heater in this case) to vaporize a portion of the source liquid to generate the aerosol. The airflow passes through the air passage, and combines with the aerosol in the region around the aerosol generating region, and the resulting aerosol then travels along the air channel connecting from the aerosol generating region to the mouthpiece 35 to be inhaled by a user. The cartomizer 30 may be detached from the body 20 and disposed of when the supply of source liquid is exhausted (and replaced with another cartomizer if so desired). Alternatively, the cartomizer 30 may be refillable.

It will be appreciated the e-cigarette 10 shown in FIG. 1 is presented by way of example, and various other implementations can be adopted. For example, in some embodiments, the cartomizer 30 is provided as two separable components, namely a cartridge comprising the liquid storage region and mouthpiece 35 (which can be replaced when the liquid from the reservoir is exhausted), and a vaporizer/aerosol generating component comprising a heater (which is generally retained). In some embodiments, the aerosol generating component may itself be replaceable. As another example, the charging facility may connect to an additional or alternative power source, such as a car cigarette lighter socket.

Figure 2:
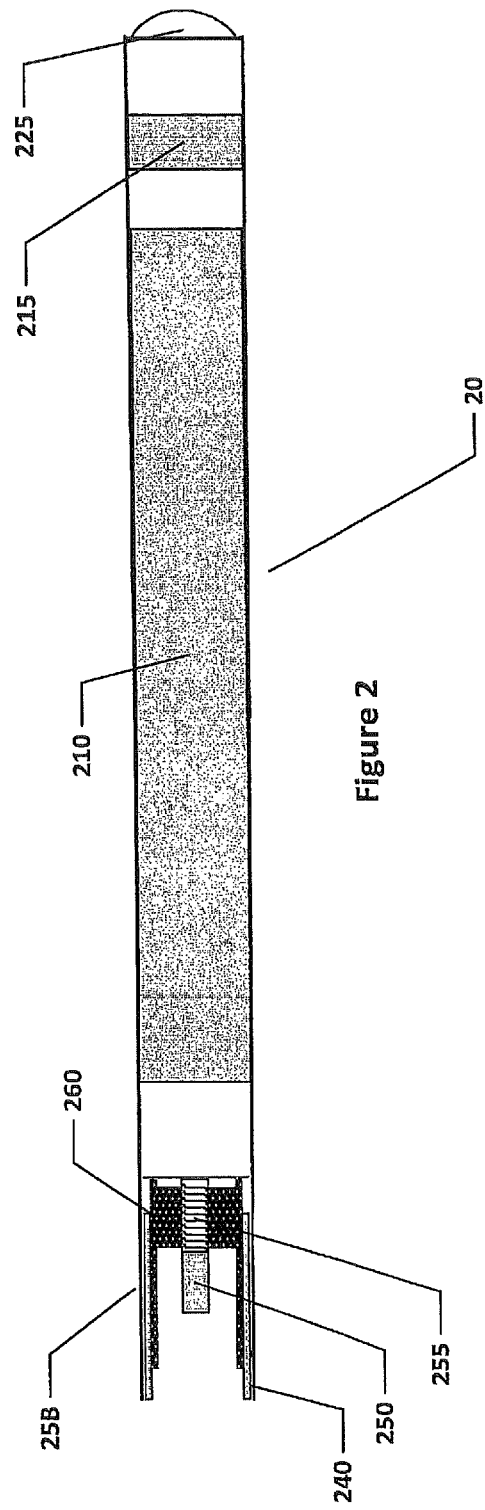

FIG. 2 is a schematic (simplified) diagram of the body 20 of the e-cigarette 10 of FIG. 1. FIG. 2 can generally be regarded as a cross-section in a plane through the longitudinal axis LA of the e-cigarette 10. Note that various components and details of the body 20, e.g. such as wiring and more complex shaping, have been omitted from FIG. 2 for reasons of clarity.

As shown in FIG. 2, the body 20 includes a battery or cell 210 for powering the e-cigarette 10, as well as a chip, such as an application specific integrated circuit (ASIC) or microcontroller for controlling the e-cigarette 10. The ASIC may be positioned alongside or at one end of the battery 210. The ASIC is attached to a sensor unit 215 to detect an inhalation on mouthpiece 35 (or alternatively the sensor unit 215 may be provided on the ASIC itself). In response to such a detection, the ASIC provides power from the battery or cell 210 to the heater in the cartomizer 30 to vaporize source liquid and introduce an aerosol into the airflow which is inhaled by a user. It should be noted that the precise positioning of the ASIC/sensor within the body 20 is not strictly limited.

The body 20 further includes a cap 225 to seal and protect the far (distal) end of the e-cigarette 10. There is an air inlet hole provided in or adjacent to the cap 225 to allow air to enter the body 20 and flow past the sensor unit 215 when a user inhales on the mouthpiece 35. This airflow therefore allows the sensor unit 215 to detect the user inhalation and so activate the aerosol generating component of the e-cigarette 10.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B. It may be that when the sensor 215 is located at the opposite end of the body 20 relative to the cap 225, the body 20 includes one or more air inlet holes provided in or adjacent to connector 25B to allow air to enter the body 20 and flow past the sensor unit 215 when a user inhales on the mouthpiece 35.

Figure 3:
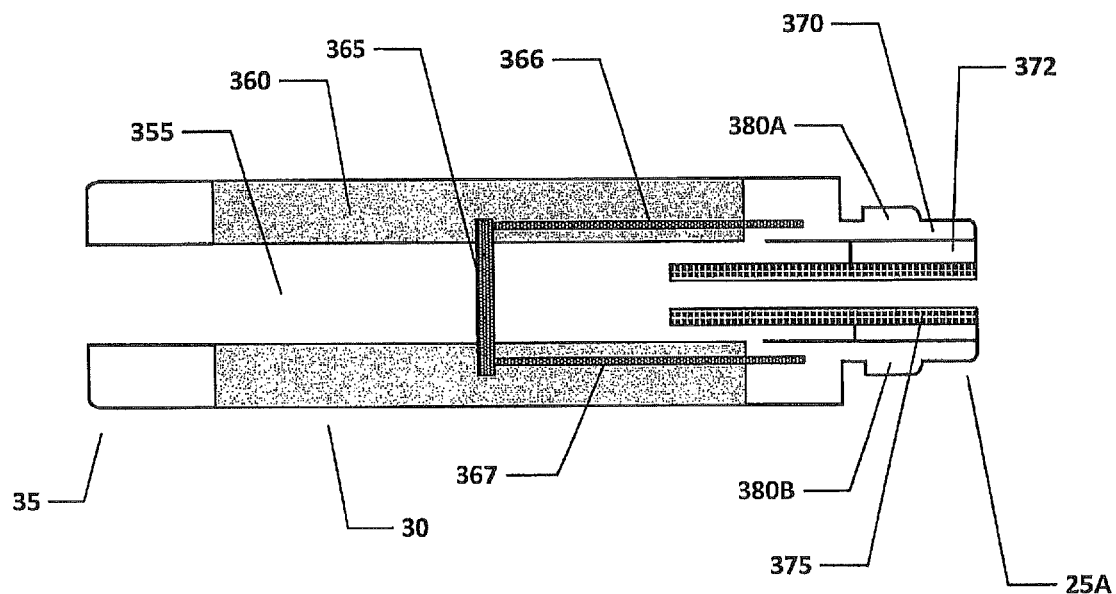

FIG. 3 is a schematic diagram of the cartomizer 30 of the e-cigarette 10 of FIG. 1 in accordance with some embodiments. FIG. 3 can generally be regarded as a cross-section in a plane through the longitudinal axis LA of the e-cigarette 10. Note that various components and details of the body 20, e.g. such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer to the body 20.

A liquid storage region 360 is provided around the air passage 335. This storage region 360 may be implemented, for example, by providing cotton or foam soaked in source liquid. Alternatively, it may be a simple reservoir which contains the source liquid in a free state, i.e. not held within a wadding, matrix or the like. The cartomizer 30 also includes a heater 365 for heating liquid from the storage region 360 to generate an aerosol to flow through air passage 355 and out through an opening in the mouthpiece 35 in response to a user inhaling on the e-cigarette 10. The heater 365 is powered through lines 366 and 367, which are in turn connected to opposing polarities (positive and negative, or vice versa) of the battery 210 via connector 25A (the details of the wiring between the power lines 366 and 367 and connector 25A are omitted from FIG. 3).

The connector 25A includes an inner electrode 375, which may be made of a metal suitable for conducting electrical current. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring 372 is surrounded by the cartomizer connector 370, which may be made of a suitable metal which is able to conduct electricity. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer via supply lines 366 and 367 as appropriate.

In one embodiment, the connector 25A is a metallic component having a coating comprising silver and/or gold. In one embodiment, the inner electrode 375 is a metallic component having a coating comprising silver and/or gold. In one embodiment, the cartomizer connector 370 is a metallic component having a coating comprising silver and/or gold. In one embodiment, one or more of the connector 25A, the inner electrode 375, and the cartomizer connector 370 are metallic components having a coating comprising silver and/or gold.

In one embodiment, one, two, three, four, five, six, or every metallic component of the aerosol provision cartridge which is upstream of the aerosol generating chamber (relative to the airflow entering said chamber) and which is outside of the liquid storage region and aerosol generating region has a coating comprising gold and/or silver.

In one embodiment, every metallic component of the aerosol provision cartridge which is upstream of the aerosol generating chamber (relative to the airflow entering said chamber) and which is outside of the liquid storage region and aerosol generating region has a coating comprising gold and/or silver.

In one embodiment, every metallic component of the aerosol provision cartridge outside of the liquid storage region and aerosol generating region has a coating comprising gold and/or silver.

In one embodiment, it may be desirable to ensure that any metallic components that are in contact with airflow through the device are coated with a coating comprising gold and/or silver. In one embodiment, the surface of one or more of metallic components of the aerosol provision cartridge which is in contact with the airflow through the device is coated with a coating comprising gold and/or silver.

In another embodiment, it may be desirable to ensure that one or more metallic components are in contact with the airflow through the aerosol provision cartridge, and are located upstream of an aerosol generating component and entirely outside of a liquid storage region, wherein at least one of the metallic components has a coating comprising at least one of silver or gold.

The cartomizer connector 370 is provided with two lugs or tabs 380A, 380B, which extend in opposite directions away from the longitudinal axis of the e-cigarette 10. These tabs 380A, 380B are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
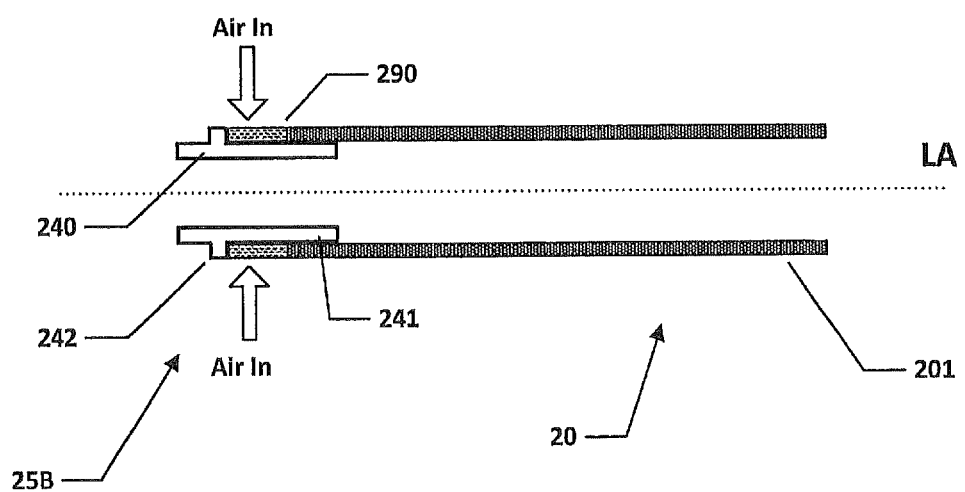

FIG. 4 is a schematic diagram of certain details of the connector 25B at the end of the body 20 in accordance with some embodiments (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar.

The body connector 240 extends from this external housing 201 of the body 20. The body connector as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, the majority of air that enters the device when a user inhales flows through collar 290 and body connector 240 as indicated by the two arrows in FIG. 4.

Figure 6:
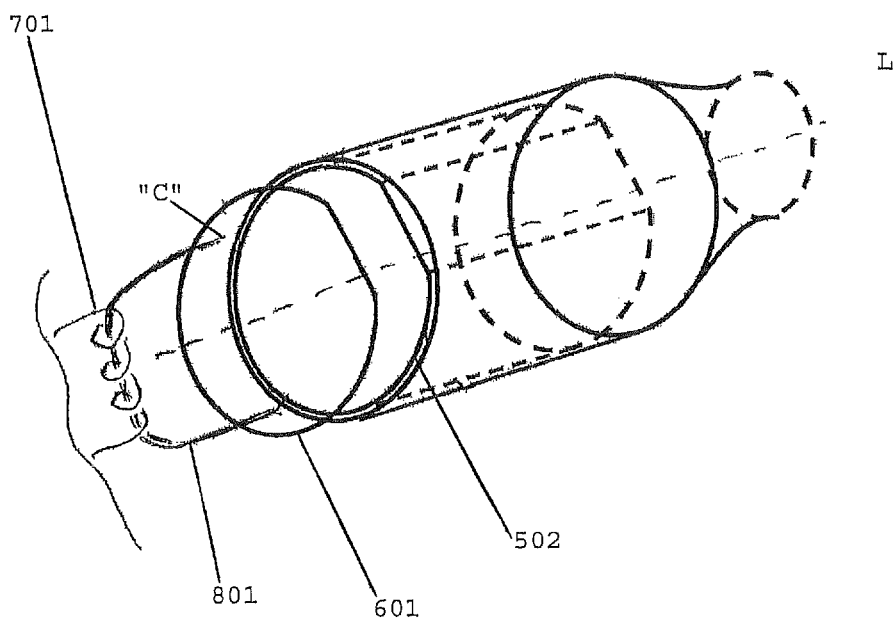

FIGS. 5A to 5E schematically represent in perspective view some aspects of part an aerosol provision/provision cartridge 500 according to some other embodiments. In particular, FIG. 5A schematically represents a first component comprising a liquid storage region component 502 and FIG. 5B schematically represents a second component 510 comprising part of a housing for the aerosol provision cartridge 500. These two components of the aerosol provision cartridge 500 are shown separately in FIGS. 5A and 5B for ease of representation, whereas in normal use these two components are assembled together as schematically represented in FIG. 5C. In the assembled state for this particular design of aerosol provision system, the liquid storage region component 502 is fitted inside the housing component 510. It will be appreciated the aerosol provision cartridge 500 will be configured to be connected to an aerosol provision device (similar to the body 20 of the e-cigarette 10 described above) in order to form an aerosol provision system. Such an aerosol provision device typically comprises a power source such as, for example, a rechargeable power source, and an input means (such as a pressure sensor or button) such that when the input means is activated by the user power is supplied from the power source to the aerosol generating component in the aerosol provision cartridge. Such other features of the aerosol provision system may be provided in accordance with conventional techniques. More generally, it will be appreciated that aspects and features of aerosol provision systems described herein may be implemented in accordance with any established techniques apart from where modified in accordance with the embodiments described herein.

The liquid storage region component 502 comprises a liquid storage body 506 defining a liquid storage region. The liquid storage region comprises a source liquid from which an aerosol is to be generated. The base of the liquid storage component is open and cooperates with membrane 601 and optionally also liquid distributing component 602. Thus, it will be appreciated that both membrane 601 and component 602 may be dimensioned to be received within the opening of the liquid storage component 502, and they may further form an interference fit with the inner wall of the liquid storage component 502.

The membrane 601 is positioned between the liquid storage region and an aerosol generating region of the system (not shown in FIG. 5). The membrane 601 allows for the source liquid contained in the liquid storage region to be fluidly communicated to the aerosol generating region of the system.

In this regard, the presence of the membrane typically results in a reduced "flow" of liquid compared to the "direct flow" that is seen in other systems of the prior art. The particular construction of the membrane need not be particularly limited, provided that it allows for the source liquid contained within the liquid store to be transferred to the aerosol generating region. It is also generally preferred if the membrane has a degree of heat resistance. In one embodiment, the membrane is formed from a porous material. In one embodiment, the membrane is formed from a porous ceramic material. In one embodiment, the membrane is formed from ceramic fibers. In this regard, ceramic fibers are known to be heat resistant and yet also provide a degree of porosity owing to their structure. Ceramic fibers may also be known as "high-temperature insulation wool" (HTIW). High-temperature insulation wool is an accumulation of fibers of different lengths and diameters, produced synthetically from mineral raw materials. The raw mineral materials are typically melted and then processed into fibers which are then formed into the final material. Different types of HTIW may be available, such as alkaline earth silicate wool, alumina silicate wool, and poly-silicate wool. Alumino silicate wool, also known as "refractory ceramic fiber" (RCF), are amorphous fibers produced by melting a combination of $Al_2O_3$ and $SiO_2$, usually in a weight ratio of about 50:50. In one embodiment, the membrane is formed from an alumina silicate wool. In one embodiment, the alumina silicate wool has a $Al_2O_3$ content of from 48 to 54% and a $SiO_2$ content of from 46 to 52%. Other raw materials, such as $Fe_2O_3$ may also be present in minor amounts. The skilled person is aware of the various considerations for producing high temperature insulation wool. In this regard, a suitable high temperature insulation wool may be obtained from Zibo Dingrong High-Temperature Materials Co., Ltd, Zibo City, Shandong Province, China.

The dimensions of the membrane itself are not particularly limited. Typically, the thickness of the membrane may be in the range 0.1 mm to 2 mm. In one embodiment, the thickness of the membrane may be in the range 0.1 to 1 mm. In one embodiment, the thickness of the membrane may be in the range 0.5 to 1.5 mm. In one embodiment, the thickness of the membrane may be in the range 0.5 to 1 mm.

The shape of the membrane may not be particularly limited. Typically, the membrane has a shape which conforms to the general cross-sectional shape of the liquid storage region. For example, as shown in FIG. 5D, the membrane has a shape which corresponds to the cross-sectional profile of the liquid storage region of liquid storage component 502. Such a shape helps to ensure that an interference/friction fit can be established with the inner walls of the liquid storage component. The membrane is generally planar.

However, it may in some circumstances be non-planar where such a configuration is necessary. For example, it may be that the membrane is tubular with the source liquid being stored in a storage region radially outward of the membrane, with the aerosol generating region, including aerosol generating component, being disposed radially inwardly of the tubular membrane.

In some embodiments, at the interface between the aerosol generating region and the liquid storage region, there may be a membrane support (not shown). This membrane support is generally rigid and serves to support the membrane from its underside (the side projecting towards the aerosol generating region). The membrane support is typically metal, and in some cases is produced from stainless steel. The grade of stainless steel used for the membrane support is not particularly limited, and it may be selected from 304L, 316L etc. The membrane support typically spans the liquid provision region of the membrane. In other words, where the membrane is generally circular, the membrane support spans substantially the entire diameter of the membrane. In this regard, the membrane support is typically "I" shaped in that it has a central linear section capped by two substantially linear bars formed at substantially right angles to the central linear section.

The aerosol generating region comprises an aerosol generating component, such as a heater. In some embodiments, the heater takes the form of a wire 701, which may also be coiled. The coiled wire may have a wick 801 running through the longitudinal axis formed by the turns of the coil. This wick may then contact the membrane at point "C" shown for example in FIG. 6 so as to draw liquid from the membrane onto or near the wire. In an alternative embodiment, the heater can take the form of a substantially sheet-like porous member.

As discussed above, a liquid distribution component 602 may optionally be present in the system between the membrane and the liquid storage region. The liquid distribution component 602 may have the function of providing more controlled wetting of the membrane. Thus, the component 602 has one or more through holes 603 which allow for the source liquid to flow from the liquid storage region onto the membrane. The membrane and the liquid distribution component may generally be disposed such that their central point is in-line with the central longitudinal axis of the system. In this regard, such a configuration (showing the membrane only) is shown in FIG. 6. The general configuration of the liquid distribution component 602 (if present) may be similar to that of the membrane. Thus it may have a corresponding cross-sectional profile and be generally planar.

The reservoir body 506 is generally in the form of a circular cylinder with a flat face 508 running longitudinally along one side. The reservoir body 506 may be formed in accordance with conventional techniques, for example comprising a molded plastics material.

The housing component 510 is generally tubular and circularly symmetric. The housing component 510 comprises a main housing component 512 and a mouthpiece component 514. These may be formed separately or integrally. The main housing component 512 and mouthpiece component 514 may be formed in accordance with conventional techniques, for example comprising extruded aluminum or molded plastic. The main housing component 512 comprises a generally cylindrical tube having an interior dimension conforming to the exterior dimension of the liquid storage component 502. Thus the liquid storage component 502 can be received within the housing component 510 in a close-fitting arrangement, as schematically represented in FIG. 5C. It will be appreciated the housing component 510 will in general extend further than represented in FIG. 5C so as to generally enclose the aerosol generator 504. The mouthpiece component 514 of the housing component 510 is contoured to provide a transition from the shape of the main housing component 512 to a shape which is ergonomically suited to be received by a user's lips during use. The mouthpiece component 514 includes an opening 516 at the end through which a user may inhale aerosol generated by the aerosol source.

As can be seen from the schematic representation in FIG. 5C, when the liquid storage component 502 is inserted into the housing component 510, the provision of the flat surface 508 creates a spacing between the outside wall of the reservoir body 506 and the inside wall of the housing component 510. This region where the first component 502 and the second component 510 of the aerosol provision system 500 are spaced apart thereby defines part of an air channel 520 connecting from the vicinity of the aerosol generator 504 to the opening 516. Other parts of the air channel are defined by the interior of the housing 510 that does not surround the liquid storage component 502 adjacent to the mouthpiece 514 and the interior surface of the mouthpiece 514. In general there may be further structural elements of the aerosol provision system in these regions to define the air channel 520. For example, flow restrictors and/or baffles and/or switchbacks may be provided to govern the airflow in accordance with conventional techniques.

As discussed briefly above, FIG. 6 shows an exploded view of the aerosol provision system 500 and also indicates the presence of a heating wire 701 as the aerosol generating component, and a wick 801 that extends through the wire (which in this configuration is coiled). The wire 701 and wick 801 sit in a housing of the aerosol generating region (not shown). The wire 701 is electrically connected through (optionally via/through the housing of the aerosol generating region) to a power source in the body 20 of the system. As will be apparent from FIG. 6, source liquid is stored with the liquid storage region formed within the liquid storage component 502. The membrane 601 then separates the liquid storage region (and thus the source liquid) from the aerosol generating region containing the wire 701 and the wick 801. The membrane 601 serves as a barrier to the "free flow" of source liquid into the aerosol generating region. However, the membrane 601 is configured to fluidly communicate the liquid storage region with the aerosol generating region. In other words, the source liquid is able to travel across the membrane 601 from one side to the other. Wick 801 is typically in contact with the underside of the membrane 601 and thus serves to draw the source liquid that has traveled across the membrane 601 towards the heating wire. The wick 901 itself can be made of any suitable material known in the art which has a high degree of heat resistance and is capable of transporting a liquid, e.g. through capillary action. In one embodiment, the wick 801 is secured to the underside of the membrane. This may be achieved through the use of an adhesive, or through physical means (such as a clamp etc.). Such an arrangement ensures good contact with the underside of the membrane. Points "C" shown in FIG. 6 illustrate points of contact between the wick 801 and the underside of the membrane 601.

The aerosol provision system 500 may also comprise components that correspond substantially to those described earlier with respect to e-cigarette 10. In this regard, aerosol provision system 500 may additionally comprise a screw component and an inner electrode. In one embodiment, the screw component is a metallic component having a coating comprising silver and/or gold. In one embodiment, the inner electrode is a metallic component having a coating comprising silver and/or gold. In one embodiment, both the screw component and the inner electrode are metallic components independently having a coating comprising gold and/or silver.

In one embodiment, the screw component is located outside of the aerosol generating region. In one embodiment, the inner electrode is located outside of the aerosol generating region.

In one embodiment, one, two, three, four, five, six, or every metallic component of the aerosol provision cartridge which is upstream of the aerosol generating chamber (relative to the airflow entering said chamber) and which is outside of the liquid storage region and aerosol generating region has a coating comprising gold and/or silver.

In one embodiment, every metallic component of the aerosol provision cartridge which is upstream of the aerosol generating chamber (relative to the airflow entering said chamber) and which is outside of the liquid storage region and aerosol generating region has a coating comprising gold and/or silver.

In one embodiment, every metallic component of the aerosol provision cartridge outside of the liquid storage region and aerosol generating region has a coating comprising gold and/or silver.

The coated metallic components referred to herein generally have a coating comprising gold and/or silver. In the context of the present invention, a "coating" refers to a outer layer of coating material that may extend over the entire surface of the base metallic component. Alternatively, the coating may not extend over the entire surface of the base metallic component, and instead be limited to discrete areas. Although the term "coating" is used in the present invention, the term "plating" is deemed to be equivalent.

Coating such components has surprisingly led to aerosols that are more acceptable to users. This is explained with further reference to the examples below. Generally, the coating used to coat the metallic components referred to herein comprise at least one of gold and/or silver. In one embodiment, one or more metallic components can comprise more than one metallic component coated with the same coating, or alternatively, the one or more metallic components can comprise more than one metallic component coated with a different coating. In one embodiment, the metallic components referred to herein have a coating comprising at least gold. In one embodiment, the metallic components referred to herein have a coating comprising at least silver. In one embodiment, the metallic components referred to herein have a coating comprising a gold alloy. In one embodiment, the coating comprises gold in an amount of about 99% w/w, with reference to the weight of the coating. In one embodiment, the coating comprises gold in an amount of greater than 99% w/w, with reference to the weight of the coating. In one embodiment, the coating comprises gold in an amount of about 99.7% w/w, with reference to the weight of the coating. In one embodiment, the coating comprises gold in an amount of about 99.9% w/w, with reference to the weight of the coating. Suitable gold containing coatings (also referred to as platings) are defined under standards such as Mil-G-45204, ASTM B488 or AMS 2422. Suitable silver containing coatings (also referred to as platings) are defined under standards such as QQ-S-365, ASTM B700, AMS 2410, AMS 2411 and AMS 2412.

The thickness of the coating on the metallic components must be such that the base metal of the metallic component is not exposed. In one embodiment, the coating on the metallic component(s) is at least 0.001 mm thick. In one embodiment, the coating on the metallic component(s) is at least 0.002 mm thick. In one embodiment, the coating on the metallic component(s) is at least 0.003 mm thick. In one embodiment, the coating on the metallic component(s) is at least 0.004 mm thick. In one embodiment, the coating on the metallic component(s) is at least 0.005 mm thick. In one embodiment, the coating on the metallic component(s) is from 0.001 mm to about 0.005 mm thick. In one embodiment, the coating on the metallic component(s) is from 0.001 mm to about 0.004 mm thick. In one embodiment, the coating on the metallic component(s) is from 0.001 mm to about 0.003 mm thick. In one embodiment, the coating on the metallic component(s) is from 0.001 mm to about 0.002 mm thick. In one embodiment, the coating on the metallic component(s) is from 0.002 mm to about 0.005 mm thick. In one embodiment, the coating on the metallic component(s) is from 0.003 mm to about 0.005 mm thick. In one embodiment, the coating on the metallic component(s) is from 0.004 mm to about 0.005 mm thick. In one embodiment, the coating on the metallic component(s) is about 0.004 mm thick.

The metallic components of the invention are typically brass or stainless steel. In one embodiment, the coated metallic components are brass, coated with a coating comprising gold and/or silver.

In one embodiment, the source liquid comprises nicotine and benzoic acid, and the metallic components are brass, coated with a coating comprising gold.

The general operating principles of the aerosol provision system 500 schematically represented in FIGS. 5A to 5E and FIG. 6 may be similar to those described above for the aerosol provision system represented in FIGS. 1 to 4. Thus, in use, a user sucks on the mouthpiece 514, which leads to air being drawn into the interior of the aerosol provision system 500 through inlet openings in the aerosol provision system (not shown in the figures). A controller of the aerosol provision system is configured to detect the inlet of air, for example based on a change in pressure, and activate the aerosol generating component in response thereto. Thus, an aerosol of the source liquid is generated. As air is drawn through the aerosol provision system it carries some of the aerosol through the air channel 520 to the opening 516 in the mouthpiece 514. In this regard, the housing of the aerosol generating region generally has a cross-section that conforms to the cross-section of housing component 510. This allows any aerosol formed in the aerosol generating region to access channel 520.

In some embodiments, the source liquid comprises nicotine, a carrier and one or more acids. The carrier of the source liquid may be any suitable solvent such that the source liquid can be vaporized for use. In one aspect the solvent is selected from glycerol, propylene glycol (PG) and mixtures thereof. In one aspect the solvent is at least glycerol. In one aspect the solvent consists essentially of glycerol. In one aspect the solvent consists of glycerol. In one aspect the solvent is at least propylene glycol. In one aspect the solvent consists essentially of propylene glycol. In one aspect the solvent consists of propylene glycol. In one aspect the solvent is at least a mixture of propylene glycol and glycerol. In one aspect the solvent consists essentially of a mixture of propylene glycol and glycerol. In one aspect the solvent consists of a mixture of propylene glycol and glycerol.

The carrier of the source liquid may be present in any suitable amount. In one aspect the carrier is present in an amount of 1 to 98 wt % based on the source liquid. In one aspect the carrier is present in an amount of 5 to 98 wt % based on the source liquid. In one aspect the carrier is present in an amount of 10 to 98 wt % based on the source liquid. In one aspect the carrier is present in an amount of 20 to 98 wt % based on the source liquid. In one aspect the carrier is present in an amount of 30 to 98 wt % based on the source liquid. In one aspect the carrier is present in an amount of 40 to 98 wt % based on the source liquid. In one aspect the carrier is present in an amount of 50 to 98 wt % based on the source liquid. In one aspect the carrier is present in an amount of 60 to 98 wt % based on the source liquid. In one aspect the carrier is present in an amount of 70 to 98 wt % based on the source liquid. In one aspect the carrier is present in an amount of 80 to 98 wt % based on the source liquid. In one aspect the carrier is present in an amount of 90 to 98 wt % based on the source liquid. In one aspect the carrier is present in an amount of 1 to 90 wt % based on the source liquid. In one aspect the carrier is present in an amount of 5 to 90 wt % based on the source liquid. In one aspect the carrier is present in an amount of 10 to 90 wt % based on the source liquid. In one aspect the carrier is present in an amount of 20 to 90 wt % based on the source liquid. In one aspect the carrier is present in an amount of 30 to 90 wt % based on the source liquid. In one aspect the carrier is present in an amount of 40 to 90 wt % based on the source liquid. In one aspect the carrier is present in an amount of 50 to 90 wt % based on the source liquid. In one aspect the carrier is present in an amount of 60 to 90 wt % based on the source liquid. In one aspect the carrier is present in an amount of 70 to 90 wt % based on the source liquid. In one aspect the carrier is present in an amount of 80 to 90 wt % based on the source liquid.

In one aspect the source liquid further comprises water. The water may be present in any suitable amount. In one aspect water is present in an amount of 1 to 50 wt % based on the source liquid. In one aspect water is present in an amount of 5 to 50 wt % based on the source liquid. In one aspect water is present in an amount of 10 to 50 wt % based on the source liquid. In one aspect water is present in an amount of 20 to 50 wt % based on the source liquid. In one aspect water is present in an amount of 1 to 40 wt % based on the source liquid. In one aspect water is present in an amount of 5 to 40 wt % based on the source liquid. In one aspect water is present in an amount of 10 to 40 wt % based on the source liquid. In one aspect water is present in an amount of 20 to 40 wt % based on the source liquid. In one aspect water is present in an amount of 1 to 30 wt % based on the source liquid. In one aspect water is present in an amount of 5 to 30 wt % based on the source liquid. In one aspect water is present in an amount of 10 to 30 wt % based on the source liquid. In one aspect water is present in an amount of 20 to 30 wt % based on the source liquid.

In one aspect the combined amount of carrier and water in the source liquid is from 1 to 98 wt % based on the source liquid. In one aspect the combined amount of carrier and water in the source liquid is 5 to 98 wt % based on the source liquid. In one aspect the combined amount of carrier and water in the source liquid is 10 to 98 wt % based on the source liquid. In one aspect the combined amount of carrier and water in the source liquid is 20 to 98 wt % based on the source liquid. In one aspect the combined amount of carrier and water in the source liquid is 30 to 98 wt % based on the source liquid. In one aspect the combined amount of carrier and water in the source liquid is 40 to 98 wt % based on the source liquid. In one aspect the combined amount of carrier and water in the source liquid is 50 to 98 wt % based on the source liquid. In one aspect the combined amount of carrier and water in the source liquid is 60 to 98 wt % based on the source liquid. In one aspect the combined amount of carrier and water in the source liquid is 70 to 98 wt % based on the source liquid. In one aspect the combined amount of carrier and water in the source liquid is 80 to 98 wt % based on the source liquid. In one aspect the combined amount of carrier and water in the source liquid is 90 to 98 wt % based on the source liquid. In one aspect the combined amount of carrier and water in the source liquid is 1 to 90 wt % based on the source liquid. In one aspect the combined amount of carrier and water in the source liquid is 5 to 90 wt % based on the source liquid. In one aspect the combined amount of carrier and water in the source liquid is 10 to 90 wt % based on the source liquid. In one aspect the combined amount of carrier and water in the source liquid is 20 to 90 wt % based on the source liquid. In one aspect the combined amount of carrier and water in the source liquid is 30 to 90 wt % based on the source liquid. In one aspect the combined amount of carrier and water in the source liquid is 40 to 90 wt % based on the source liquid. In one aspect the combined amount of carrier and water in the source liquid is 50 to 90 wt % based on the source liquid. In one aspect the combined amount of carrier and water in the source liquid is 60 to 90 wt % based on the source liquid. In one aspect the combined amount of carrier and water in the source liquid is 70 to 90 wt % based on the source liquid. In one aspect the combined amount of carrier and water in the source liquid is 80 to 90 wt % based on the source liquid. In one aspect the combined amount of carrier and water in the source liquid is 90 to 90 wt % based on the source liquid.

The source liquid comprises an acid, such as an organic acid. In one aspect the organic acid is a carboxylic acid. The carboxylic acid may be any suitable carboxylic acid. In one aspect the organic acid is a mono-carboxylic acid. In one aspect the organic acid is selected from the group consisting of acetic acid, lactic acid, benzoic acid, levulinic acid, formic acid, citric acid, pyruvic acid, succinic acid, tartaric acid, oleic acid, sorbic acid, propionic acid, phenylacetic acid, and mixtures thereof. In one embodiment, the source liquid comprises benzoic acid. In one embodiment, the source liquid comprises levulinic acid.

In one embodiment, the total content of acid present in the source liquid is no greater than 1 mole equivalents based on the nicotine. In one embodiment, the total content of acid present in the source liquid is no greater than 0.9 mole equivalents based on the nicotine. In one embodiment, the total content of acid present in the source liquid is no greater than 0.8 mole equivalents based on the nicotine. In one embodiment, the total content of acid present in the source liquid is no greater than 0.7 mole equivalents based on the nicotine. In one embodiment, the total content of acid present in the source liquid is no greater than 0.6 mole equivalents based on the nicotine. In one aspect the total content of acid present in the source liquid is no greater than 0.55 mole equivalents based on the nicotine. In one aspect the total content of acid present in the source liquid is no greater than 0.5 mole equivalents based on the nicotine. In one aspect the total content of acid present in the source liquid is no greater than 0.45 mole equivalents based on the nicotine. In one aspect the total content of acid present in the source liquid is no greater than 0.4 mole equivalents based on the nicotine. In one aspect the total content of acid present in the source liquid is no greater than 0.35 mole equivalents based on the nicotine. In one aspect the total content of acid present in the source liquid is no greater than 0.3 mole equivalents based on the nicotine.

In one aspect the total content of acid present in the source liquid is from 0.1 to 0.6 mole equivalents based on the nicotine. In one aspect the total content of acid present in the source liquid is from 0.1 to 0.5 mole equivalents based on the nicotine. In one aspect the total content of acid present in the source liquid is from 0.2 to 0.6 mole equivalents based on the nicotine. In one aspect the total content of acid present in the source liquid is from 0.1 to 0.4 mole equivalents based on the nicotine. In one aspect the total content of acid present in the source liquid is from 0.3 to 0.6 mole equivalents based on the nicotine. In one aspect the total content of acid present in the source liquid is from 0.2 to 0.5 mole equivalents based on the nicotine. In one aspect the total content of acid present in the source liquid is from 0.3 to 0.5 mole equivalents based on the nicotine. In one aspect the total content of acid present in the source liquid is from 0.2 to 0.4 mole equivalents based on the nicotine.

Nicotine may be provided at any suitable amount depending on the desired dosage when inhaled by the user. In one aspect nicotine is present in an amount of no greater than 6 wt % based on the total weight of the source liquid. In one aspect nicotine is present in an amount of from 0.4 to 6 wt % based on the total weight of the source liquid. In one aspect nicotine is present in an amount of from 0.8 to 6 wt % based on the total weight of the source liquid. In one aspect nicotine is present in an amount of from 1 to 6 wt % based on the total weight of the source liquid. In one aspect nicotine is present in an amount of from 1.8 to 6 wt % based on the total weight of the source liquid. In one aspect nicotine is present in an amount of from 0.4 to 5 wt % based on the total weight of the source liquid. In one aspect nicotine is present in an amount of from 0.8 to 5 wt % based on the total weight of the source liquid. In one aspect nicotine is present in an amount of from 1 to 5 wt % based on the total weight of the source liquid. In one aspect nicotine is present in an amount of from 1.8 to 5 wt % based on the total weight of the source liquid. In one aspect nicotine is present in an amount of no greater than 4 wt % based on the total weight of the source liquid. In one aspect nicotine is present in an amount of from 0.4 to 4 wt % based on the total weight of the source liquid. In one aspect nicotine is present in an amount of from 0.8 to 4 wt % based on the total weight of the source liquid. In one aspect nicotine is present in an amount of from 1 to 4 wt % based on the total weight of the source liquid. In one aspect nicotine is present in an amount of from 1.8 to 4 wt % based on the total weight of the source liquid. In one aspect nicotine is present in an amount of no greater than 3 wt % based on the total weight of the source liquid. In one aspect nicotine is present in an amount of from 0.4 to 3 wt % based on the total weight of the source liquid. In one aspect nicotine is present in an amount of from 0.8 to 3 wt % based on the total weight of the source liquid. In one aspect nicotine is present in an amount of from 1 to 3 wt % based on the total weight of the source liquid. In one aspect nicotine is present in an amount of from 1.8 to 3 wt % based on the total weight of the source liquid. In one aspect nicotine is present in an amount of no greater than 1.8 wt % based on the total weight of the source liquid. In one aspect nicotine is present in an amount of from 0.4 to 1.8 wt % based on the total weight of the source liquid. In one aspect nicotine is present in an amount of from 0.5 to 1.8 wt % based on the total weight of the source liquid. In one aspect nicotine is present in an amount of from 0.8 to 1.8 wt % based on the total weight of the source liquid. In one aspect nicotine is present in an amount of from 1 to 1.8 wt % based on the total weight of the source liquid. In one aspect nicotine is present in an amount of less than 1.8 wt % based on the total weight of the source liquid. In one aspect nicotine is present in an amount of from 0.4 to less than 1.8 wt % based on the total weight of the source liquid. In one aspect nicotine is present in an amount of from 0.5 to less than 1.8 wt % based on the total weight of the source liquid. In one aspect nicotine is present in an amount of from 0.8 to less than 1.8 wt % based on the total weight of the source liquid. In one aspect nicotine is present in an amount of from 1 to less than 1.8 wt % based on the total weight of the source liquid.

The source liquid may comprise a number of other components such as flavorings. The amounts of these components can generally be varied depending on the desired profile of the source liquid. In some embodiments, the flavorings are dissolved in propylene glycol and so the "flavoring" component may be understood as a combination of the PG and the active flavoring compounds. Typical flavoring components may include menthol, and other active compounds providing other sensory flavors such as cherry, smokey, etc.

The acid is typically present in the source liquid as a source of protons with which to protonate the nicotine present in the source liquid. In this regard, nicotine generally exists as a free base in which neither of its nitrogen atoms are "protonated". The inclusion of an acid in the source liquid provides a source of protons which can protonate the nicotine.

In a further aspect, there is provided an aerosol provision cartridge for use with an aerosol provision system, said cartridge comprising: a liquid storage region in fluid communication with an aerosol generating region; said aerosol generating region configured to be substantially liquid-free; and one or more metallic components, located substantially outside of the aerosol generating region and liquid storage region, wherein at least one of the said metallic components has a coating comprising silver and/or gold.

In this regard, the term an "said aerosol generating region configured to be substantially liquid-free" means that the aerosol generating region is a chamber which is substantially free of liquid during use. In other words, whilst small amounts of condensate may form in the aerosol generating region/chamber, it is intended that in normal use this part of the cartridge will not be a reservoir or store for liquid that is to be vaporized.

In one embodiment, there are no metallic components in the aerosol generating region/chamber, other than the aerosol generating component.

In a further aspect there is provided the use of a metallic component having a coating comprising gold and/or silver in an aerosol provision cartridge to stabilize and/or improve the acceptability of the aerosol to a user. In this regard, the metallic component having a coating comprising gold and/or silver is as defined with respect to the aerosol provision cartridge defined above.

In a further aspect there is provided a method of preventing the deterioration of the sensorial attributes of an aerosol produced from an aerosol provision cartridge comprising utilizing in the construction of the cartridge a metallic component having a coating comprising gold and/or silver. In this regard, the metallic component having a coating comprising gold and/or silver is as defined with respect to the aerosol provision cartridge defined above.

In a further aspect there is provided an aerosol provision system comprising an aerosol provision cartridge as defined herein, and an aerosol provision device comprising a power source and an input means. The aerosol provision device may be as defined above with regard to, for example, the body 20 described with reference to the embodiment of FIGS. 1 to 4.

Thus, described above are examples of aerosol provision systems that can help ameliorate the issues discussed above with regard to the generation of degradation products. The following examples serve to illustrate the surprising benefits of the present system.

EXAMPLES

An assessment was made of an aerosol provision system comprising metallic components having various coatings. An aerosol provision system (ePen, www.govype.com) was modified such that metallic components of the aerosol provision cartridge which were outside of the aerosol generating region/chamber and liquid storage region were coated with a range of coatings. The coatings assessed contained:
Nickel (Example 1)
Tin (Example 2)
Gold (Example 3)
Silver (Example 4)

Multiple cartridges were prepared for each example and the liquid storage region of each aerosol provision cartridge was filled with a source liquid comprising nicotine, water, glycerol and an organic acid as set out in Table 1. Thus, for each experiment, Sample 1 contained no organic acid, whereas Samples 2 and 3 contained 0.3 molar equivalents and 0.75 molar equivalents of acid respectively, relative to the nicotine in the source liquid.

TABLE 1

|  | 0 meq acid | 0.3 meq acid | 0.75 meq acid |
| --- | --- | --- | --- |
| Example 1 (nickel) | Sample 1 | Sample 2 | Sample 3 |
| Example 2 (tin) | Sample 1 | Sample 2 | Sample 3 |
| Example 3 (gold) | Sample 1 | Sample 2 | Sample 3 |
| Example 4 (silver) | Sample 1 | Sample 2 | Sample 3 |

Each sample was stored for 14 days at ambient temperature. Additionally, replicates where prepared and stored under "accelerated" conditions of elevated temperatures as follows:

1 week at 40° C.;
3 weeks at 40° C.; and
7 weeks at 40° C.

Prior to user assessment of the aerosol, an analysis was carried out of the trace metals (if any) present in the aerosol. The samples comprising metallic components with nickel, gold and silver containing coatings did not lead to unacceptable levels of metals being identified in the aerosol. The samples comprising metallic components with tin containing components had unacceptable levels of metals in the aerosol and were not used in the user assessment of the aerosol.

For the user assessment, six users were asked to rate the aerosol in terms of preference on a scale of 1 to 4, a lower score indicating a higher preference. Their preferences were recorded and the average reference provided.

Figure 7:
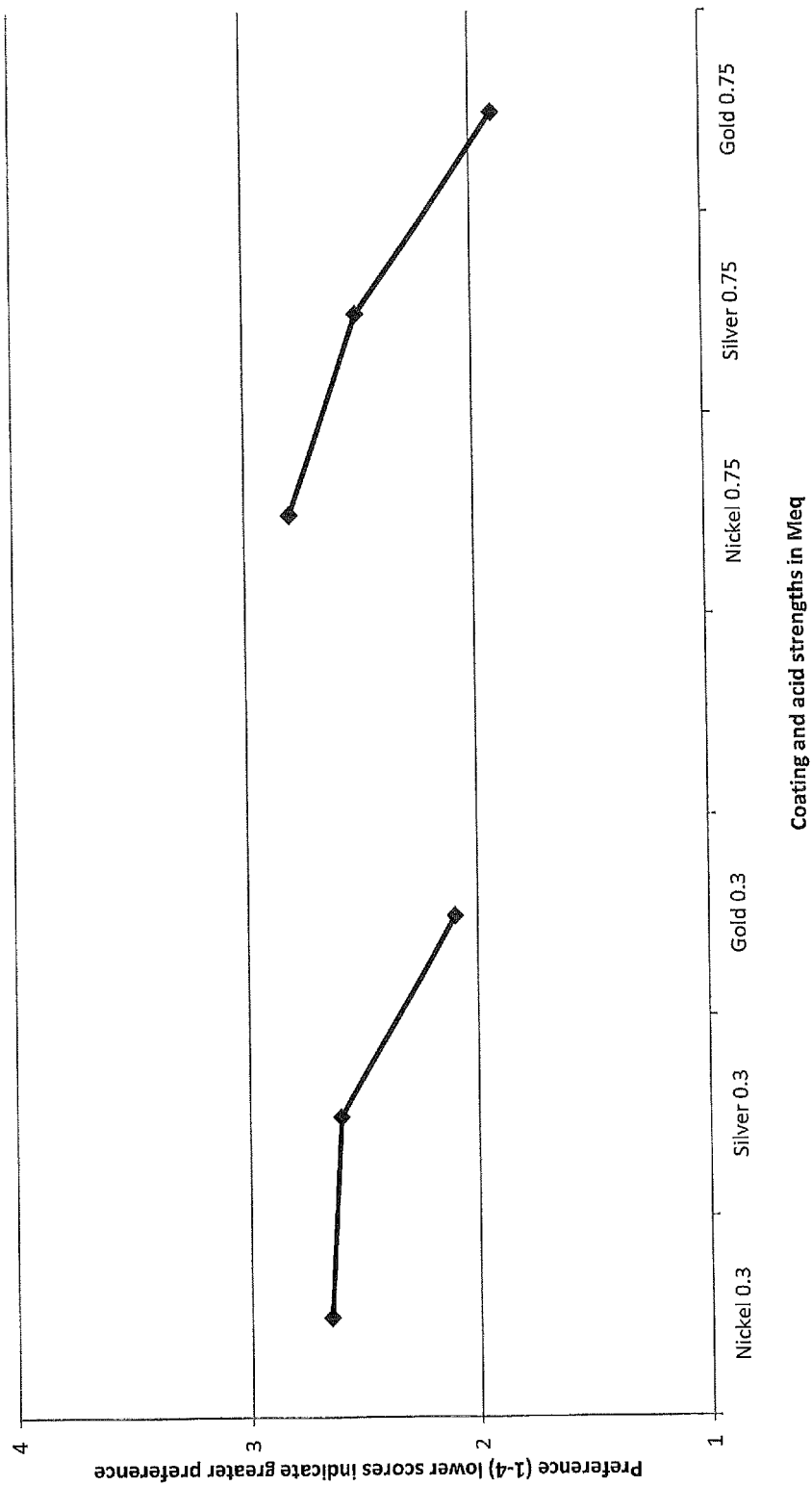

As can be seen from FIG. 7, aerosols produced from aerosol provision cartridges comprising a protonated formulation (a liquid source comprising nicotine and an acid) and metallic components outside of the aerosol generating region coated with coatings comprising nickel were generally less preferred compared to coatings comprising gold or silver. When the metallic components were coated with a coating comprising gold, the preference was greatest. Selecting specific components outside of the aerosol generating region and coating them with suitable coatings (comprising gold or silver) leads to more preferred aerosols. Without being bound in this regard, it is thought that this is the case because metallic components generally located outside of the aerosol generating region nevertheless may become exposed to source liquid. This exposure may then lead to reaction products being produced which, over time, will become entrained in the airflow through the device and become perceptible to the user. As a result of selectively coating such metallic components, the aerosol provided to the user can be stabilized and/or improved relative to systems without such selective coatings.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol provision cartridge for use with an aerosol provision system, the cartridge comprising:
a liquid storage region comprising a source liquid, the source liquid comprising nicotine and at least one acid;
an aerosol generating component in fluid communication with the liquid storage region; and
one or more metallic components, wherein the one or more metallic components are in contact with airflow through an airflow passage extending along a central longitudinal axis of the aerosol provision cartridge, and are located upstream of the aerosol generating component relative to airflow through said airflow passage and entirely outside of the liquid storage region, wherein at least one of the one or more metallic components has a coating comprising at least one of silver or gold.

2. The aerosol provision cartridge according to claim 1, wherein the one or more metallic components comprise at least one component selected from an electrode, a connecting ring and an outer housing.

3. The aerosol provision cartridge according to claim 1, wherein the one or more metallic components comprise more than one metallic component coated with the same coating.

4. The aerosol provision cartridge according to claim 1, wherein the one or more metallic components comprise more than one metallic component coated with a different coating.

5. The aerosol provision cartridge according to claim 1, wherein the at least one acid is benzoic acid.

6. The aerosol provision cartridge according to claim 5, wherein the benzoic acid is present in an amount of less than 1 meq relative to nicotine.

7. The aerosol provision cartridge according to claim 1, wherein the at least one acid is levulinic acid.

8. The aerosol provision cartridge according to claim 1, wherein the one or more metallic components are coated with a coating comprising gold.

9. The aerosol provision cartridge according to claim 8, wherein the coating comprises a gold alloy.

10. The aerosol provision cartridge according to claim 1, wherein the source liquid further comprises glycerol, propylene glycol and water.

11. The aerosol provision cartridge according to claim 10, wherein the source liquid further comprises one or more flavorings or additives.

12. The aerosol provision cartridge according to claim 1, wherein the aerosol generating component is a heater.

13. The aerosol provision cartridge according to claim 12, wherein the heater is a substantially sheet-like porous member.

14. The aerosol provision cartridge according to claim 12, wherein the heater is a wire coil.

15. An aerosol provision system comprising the aerosol provision cartridge of claim 1 and a device comprising a body section, the body section comprising a power source, a control unit and one or more input means, wherein the device is configured to supply power to the aerosol provision cartridge in order to generate an aerosol in response to input from a user.

16. The aerosol provision system of claim 15, wherein the power source is rechargeable.

* * * * *